US010172974B2

(12) United States Patent
Yang et al.

(10) Patent No.: US 10,172,974 B2
(45) **Date of Patent: *Jan. 8, 2019**

(54) ANTIMICROBIAL POLYMERS

(71) Applicant: THE PENN STATE RESEARCH FOUNDATION, University Park, PA (US)

(72) Inventors: Jian Yang, State College, PA (US); Jinshan Guo, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/409,955

(22) Filed: Jan. 19, 2017

(65) Prior Publication Data

US 2017/0202998 A1 Jul. 20, 2017

Related U.S. Application Data

(60) Provisional application No. 62/280,218, filed on Jan. 19, 2016.

(51) Int. Cl.

*C08G 63/668* (2006.01)
*A61L 26/00* (2006.01)
*C08G 63/685* (2006.01)

(52) U.S. Cl.

CPC ......... *A61L 26/0019* (2013.01); *A61L 26/008* (2013.01); *A61L 26/0066* (2013.01); *C08G 63/668* (2013.01); *C08G 63/6858* (2013.01); *A61L 2300/404* (2013.01)

(58) Field of Classification Search

None

See application file for complete search history.

(56) References Cited

U.S. PATENT DOCUMENTS

| | | | |
|---|---|---|---|
| 8,530,611 | B2 | 9/2013 | Yang et al. |
| 8,568,765 | B2 | 10/2013 | Ameer et al. |
| 8,613,944 | B2 | 12/2013 | Yang et al. |
| 10,106,647 | B2 | 10/2018 | Yang et al. |
| 2005/0063939 | A1 | 3/2005 | Ameer et al. |
| 2007/0208420 | A1 | 9/2007 | Ameer et al. |
| 2009/0093565 | A1 | 4/2009 | Yang et al. |
| 2009/0325859 | A1 | 12/2009 | Ameer |
| 2011/0124765 | A1 | 5/2011 | Yang et al. |
| 2013/0217790 | A1 | 8/2013 | Yang et al. |
| 2014/0037588 | A1 | 2/2014 | Yang et al. |
| 2014/0193356 | A1 | 7/2014 | Yang |
| 2016/0106878 | A1 | 4/2016 | Yang et al. |
| 2016/0137776 | A1 | 5/2016 | Yang et al. |
| 2016/0199541 | A1 | 7/2016 | Yang et al. |
| 2016/0311973 | A1 | 10/2016 | Yang et al. |
| 2017/0080125 | A1 | 3/2017 | Yang |
| 2017/0368377 | A1 | 12/2017 | Ameer et al. |
| 2018/0088053 | A1 | 3/2018 | Yang et al. |
| 2018/0117219 | A1 | 5/2018 | Yang et al. |

FOREIGN PATENT DOCUMENTS

| | | | |
|---|---|---|---|
| WO | 2017095816 | A1 | 6/2017 |

*Primary Examiner* — Jessica Worsham

(74) *Attorney, Agent, or Firm* — John P. Zimmer; Nexsen Pruet, PLLC

(57) ABSTRACT

In one aspect, compositions are described herein. In some embodiments, a composition described herein comprises the reaction product of (i) an alkoxylated or alkenoxylated citric acid, citrate, or ester of citric acid, and optionally a non-alkoxylated and non-alkenoxylated citric acid, citrate, or ester of citric acid, with (ii) a polyol. Additionally, in some cases, a composition described herein comprises the reaction product of (i) and (ii) above and (iii) one or more additional monomers. In some cases, the composition is cross-linked by the use of one or more oxidants such as sodium periodate ($NaIO_4$) and/or silver nitrate ($AgNO_3$), which can be reduced into a reduced oxidant that provides short-term antimicrobial activity. Such a composition can have both short-term and long-term antibiotic and antifungal activity.

20 Claims, 32 Drawing Sheets

ANTIMICROBIAL POLYMERS

CROSS REFERENCE TO RELATED APPLICATIONS

This application claims priority pursuant to 35 U.S.C. § 119(e) to U.S. Provisional Patent Application Ser. No. 62/280,218, filed on Jan. 19, 2016, which is hereby incorporated by reference in its entirety.

FIELD

This invention relates to polymeric or oligomeric compositions and methods of using such compositions and, in particular, to antimicrobial compositions comprising an alkoxylated or alkenoxylated citrate-containing polymer or oligomer.

BACKGROUND

In recent years, biodegradable polymeric materials have found increased use in a wide range of biomedical engineering applications such as tissue engineering, drug delivery, wound dressing, diagnostic imaging, and medical device applications. However, microbial proliferation, including bacterial and fungal infection, has presented major complications for the use of many previous biodegradable polymers in biomedical applications. Serious complications can include tissue destruction, premature device failure, and/or the spread of an infection from one area of a patient's body to other areas of the body. In addition, the proliferation of microorganisms can stimulate a cascade of defensive responses from the body that can themselves be life-threatening. Bacterial infection and/or fungal infection are also a major obstacle for wound healing, especially chronic wound healing.

Unfortunately, many previous biodegradable polymers cannot effectively reduce or prevent microbial proliferation, bacterial infection, and/or fungal infection. Therefore, antibiotics, antifungals, or other antimicrobial materials must often be coated onto, encapsulated within, or otherwise associated with such biodegradable polymers to inhibit bacterial and/or fungal growth. Further, such approaches to inhibiting microbial proliferation and infection can sometimes have limited effectiveness and/or result in a degradation of medical device performance. Moreover, antibiotic and antifungal properties are rarely found in the same composition. Improved antimicrobial polymers or oligomers and methods of reducing microbial proliferation are therefore desired.

SUMMARY

In one aspect, polymeric or oligomeric compositions are described herein which, in some embodiments, may provide one or more advantages compared to some other polymeric or oligomeric compositions. For example, in some embodiments, a composition described herein can reduce microbial proliferation such as bacterial proliferation and/or fungal proliferation, including without the incorporation of one or more additional antimicrobial materials such as antibacterial materials and/or antifungal materials. A composition described herein may also kill and/or reduce the proliferation of Gram-positive bacteria and Gram-negative bacteria in addition to common fungal infections. Additionally, in some instances, a composition described herein can kill and/or reduce the proliferation of microbes over a sustained period of time. Compositions described herein, in some cases, can also be used as biodegradable scaffolds or supports for tissue engineering applications, and can be used as bioadhesives for tissue/wound closure, wound dressing, and bone regeneration. Moreover, a composition described herein, in some cases, can provide antimicrobial properties without substantially compromising or degrading other desirable properties of the composition, such as one or more physicochemical properties or mechanical properties, including wet tissue adhesion.

In some embodiments, a composition described herein comprises, consists, or consists essentially of a polymer or oligomer formed from the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol or polyamine such as a dial or diamine. In some cases, a composition described herein comprises a polymer or oligomer formed from other reactants or monomers in addition to (i) and (ii) above. For example, a composition can comprise, consist, or consist essentially of a polymer or oligomer formed from the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine such as a diol/diamine, and (iii) a catechol-containing species. In other cases, a composition described herein can comprise, consist, or consist essentially of a polymer or oligomer formed from the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine such as a diol/diamine, and (iii) an alcohol/amine, an amide, carboxylic acid, or an isocyanate. In addition, in still other embodiments, a composition described herein can comprise, consist, or consist essentially of a polymer or oligomer formed from the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine and (iii) an amino acid such as an alpha-amino acid. In yet another exemplary embodiment, a composition described herein can comprise, consist, or consist essentially of a polymer or oligomer formed from the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine and (iii) a monomer comprising an alkyne moiety and/or an azide moiety.

Additionally, as described above, a composition described herein, in some instances, does not include a substantial amount of one or more antimicrobial materials other than (a) the alkoxylated or alkenoxylated (and/or non-alkoxylated and non-alkenoxylated) citrate-containing polymer of the composition, and, optionally, (b) any antimicrobial reduced oxidant species of the composition, as described further below. For example, in some embodiments, the composition does not include a substantial amount of any antibacterial and/or antifungal material other than (a) the alkoxylated or alkenoxylated (and/or non-alkoxylated and non-alkenoxylated) citrate-containing polymer of the composition, and, optionally, (b) any antimicrobial reduced oxidant species of the composition, as described further below. For example, in some instances, a composition described herein is free or substantially free of small molecule antibiotics, small molecule antifungals, and/or antimicrobial peptides (where it is to be understood that such excluded species do not include reduced oxidants described hereinbelow). Moreover, in some cases, a composition described herein is free or substantially free of metal particles such as silver nanoparticles (where it is again to be understood that such excluded metal particles do not include any reduced oxidant nanoparticles described hereinbelow). Alternatively, in other embodiments, a composition described herein can include an additional antibacterial and/or antifungal material, if desired. In such cases, the additional antibacterial and/or antifungal material can be dispersed in the polymer or oligomer of the composition. Other drugs and/or nanoparticles may also be dispersed in the polymer or oligomer of a composition described herein. In addition, in some embodiments, the polymer or oligomer of a composition described herein is crosslinked to form a polymer network.

In another aspect, methods of treating a microbial infection are described herein. In some embodiments, such a method comprises reducing microbial proliferation in a biological environment by disposing a composition described herein into or onto the biological environment. A microbial infection treated by such a method can be a bacterial infection and/or a fungal infection. In certain cases, the microbial infection comprises both a bacterial and a fungal infection. In such instances, the method can comprise reducing bacterial and/or fungal proliferation within the environment by at least about 10%, at least about 30%, or at least about 50% or killing at least about 10%, at least about 30%, or at least about 50% of the bacterial infection and/or the fungal infection. Further, the biological environment may be on or in a living patient. For example, in some embodiments, the biological environment is a surface of the living patient's skin. In other cases, the biological environment is a diabetic ulcer on or in the living patient. Moreover, any composition described herein may be used in a method described herein. For example, in some cases, the composition comprises, consists, or consists essentially of a polymer or oligomer formed from the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine such as a dial/diamine and, optionally, with one or more additional monomers or reactants, as described further herein.

These and other embodiments are described in more detail in the detailed description which follows.

DETAILED DESCRIPTION

Figure 1A:
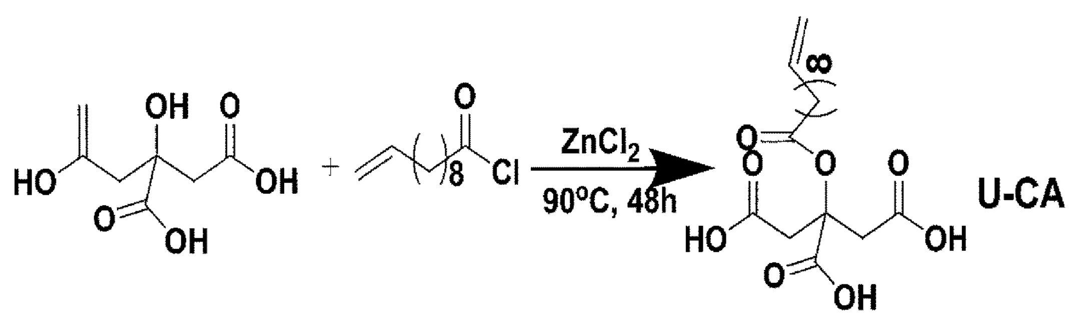
FIGS. 1A and 1B each illustrate a scheme for the preparation of alkoxylated or alkenoxylated citrate-containing polymers according to some embodiments described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Compositions

In one aspect, compositions are described herein. In some embodiments, a composition described herein comprises, consists, or consists essentially of one or more alkoxylated or alkenoxylated citrate-containing polymers or oligomers. Additionally, in some embodiments, a composition described herein does not include a substantial amount of any antimicrobial material, such as an antibacterial and/or antifungal material, other than the one or more alkoxylated or alkenoxylated citrate-containing polymers of the composition. For example, in some instances, an antimicrobial composition described herein is free or substantially free of antibiotics, antifungals, antimicrobial peptides, and/or antimicrobial inorganic compositions such as metal particles. Antibiotics can include bactericidal materials such as penicillins, cephalosporins, polymyxins, rifamycins, lipiarmycins, quinolones, and sulfonamides. Antibiotics can also include bacteriostatic materials such as macrolides, lincosamides and tetracyclines or cyclic lipopeptides, glycylcyclines, oxazolidinones, and lipiarmycins. Antifungals can include fungicidal materials such as amphotericin B, azole antifungals, echinocandins, or flucytosine. A composition that is "substantially free" of the foregoing materials, for reference purposes herein, can comprise less than about 2 weight percent, less than about 1 weight percent, less than about 0.5 weight percent, less than about 0.1 weight percent, or less than about 0.05 weight percent of the foregoing materials, based on the total weight of the composition.

Additionally, it is to be understood that the above-described antimicrobial, antibacterial, and/or antifungal materials, which can be excluded from compositions described herein, do not include materials that serve significant functions in the compositions, in addition to acting as antimicrobial, antibacterial, and/or antifungal agents. For example, the above-described compositions that do not include a substantial amount of antimicrobials, antibacterials, and/or antifungals, and even those that are free or substantially free of small molecule antibiotics, small molecule antifungals, antimicrobial peptides, and/or metal particles such as silver nanoparticles, may still contain certain functional components that also act as antimicrobial, antibacterial or antifungal agents, as described further below. Examples of such functional components can include cross-linking agents or initiators. Moreover, as described further below, the cross-linking agents or initiators may act as an antimicrobial, an antibacterial and/or an antifungal in the state in which they are initially present in or added to the composition (i.e., in an as-added state), and/or in some other state (e.g., as reduction or oxidation product(s) of the material in the as-added state).

Any alkoxylated or alkenoxylated citrate-containing polymer or oligomer not inconsistent with the objectives of the present disclosure may be used in a composition described herein. An "alkoxylated or alkenoxylated citrate-containing polymer," for reference purposes herein, is formed from a polymer or oligomer comprising an alkoxylated or alkenoxylated citrate moiety. In some cases, the alkoxylated or alkenoxylated citrate moiety is present in the backbone or main chain of the polymer. The alkoxylated or alkenoxylated citrate moiety may also be present in a pendant or side group or chain of the polymer. In some embodiments, the alkoxylated or alkenoxylated citrate moiety is a repeating unit of the polymer or is formed from a repeating unit of the polymer. Further, an "alkoxylated or alkenoxylated citrate moiety," for reference purposes herein, comprises a moiety formed from a monomer having the structure of Formula (A1):

(A1)

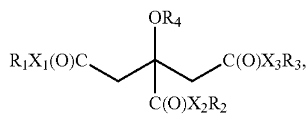

wherein $X_1$, $X_2$, and $X_3$ are each independently —O— or —NH—;

$R_1$, $R_2$, and $R_3$ are independently —H, a C1 to C22 alkyl or alkenyl group such as $—CH_3$ or $—CH_2CH_3$, or;

$R_4$ is $—C(O)R_5$;

$R_5$ is a C1 to C22 or C4 to C22 alkyl or alkenyl group; and $M^+$ is a monovalent metal cation such as $Na^+$ or $K^+$, or a divalent metal cation such as $Ca^{2+}$ or $Mg^{2+}$.

Further, it is to be understood that a "C1 to Cn" alkyl or alkenyl group refers to an alkyl or alkenyl group having 1 to n carbon atoms. The foregoing monomer can be referred to as an alkoxylated or alkenoxylated citric acid, citrate, or ester or amide of citric acid. Additionally, when the foregoing monomer is incorporated into the polymer as an alkoxylated or alkenoxylated citrate moiety, at least one of $R_1$, $R_2$, and $R_3$ is a point of attachment to the remainder of the polymer. It is to be understood that, as denoted in Formula (A1) and as described further hereinbelow, an alkyl or alkenyl moiety can be included in the $R_4$ position through alkoxylation or alkenoxylation of a citric acid, citrate, or citric acid ester or amide. Not intending to be bound by theory, it is believed that fatty acids with alkyl or alkenyl moieties such as described herein may exhibit antifungal properties due to their ability to insert into and disrupt the lipid bilayer of the fungus.

In some cases, a polymer of a composition described herein comprises the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine such as a diol/diamine. The optionally reacted non-alkoxylated and non-alkenoxylated citric acid, citrate, or ester/amide of citric acid may have the structure of Formula (A2):

(A2)

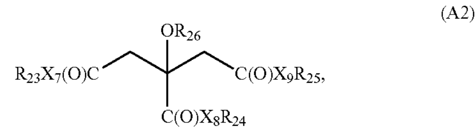

wherein $X_7$, $X_8$, and $X_9$ are each independently —O— or —NH—;

wherein $R_{23}$, $R_{24}$, and $R_{25}$ are independently —H, a C1 to C22 alkyl or alkenyl group such as $—CH_3$ or $—CH_2CH_3$, or $M^+$;

$R_{26}$ is —H or $M^+$; and $M^+$ is a monovalent metal cation such as $Na^+$ or $K^+$. For example, a monomer of Formula (A2) may be citric acid.

Non-limiting examples of polyols/polyamines suitable for use in some embodiments described herein include C2-C20, C2-C12, or C2-C6 aliphatic alkane diols/diamines, including α, ω-n-alkane diols/diamines, or α,ω-alkene diols/diamines. For instance, in some cases, a polyol/polyamine comprises 1,4-butanediol/diamine, 1,6-hexanediol/diamine, 1,8-octanediol/diamine, 1,10-decanediol/diamine, 1,12-dodecanediol/diamine, 1,16-hexadecanediol/diamine, or 1,20-icosanediol/diamine. Branched α,ω-alkane diols/diamines or α,ω-alkene diols/diamines can also be used. Additionally, a polyol/polyamine can also be an aromatic diol/diamine. Further, in some embodiments, a polyol/polyamine comprises a poly(ethylene glycol) (PEG) or poly(propylene glycol) (PPG) having terminal hydroxyl or amine groups. Any such PEG or PPG not inconsistent with the objectives of the present disclosure may be used. In some embodiments, for instance, a PEG or PPG has a weight average molecular weight between about 100 and about 5000 or between about 200 and about 1000.

In some embodiments, the polyol/polyamine may have the structures represented by Formula (B1) and/or Formula (B2):

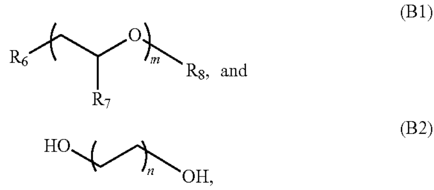

wherein $R_6$ is —H, —NH, —OH, —$OCH_3$, —$OCH_2CH_3$, —$CH_3$, or —$CH_2CH_3$;
$R_7$ is —H or a C1 to C22 alkyl or alkenyl group such as —$CH_3$;
$R_8$ is —H, —$CH_3$, —$CH_2CH_3$, a C3 to C22 alkyl or alkenyl group, —$CH_2CH_2OH$, or —$CH_2CH_2NH_2$; and
n and m are independently integers ranging from 1 to 100 or 1 to 20.
For example, in some cases, the polyol or polyamine has the structure represented by Formula (B3):

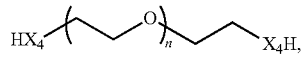

wherein $X_4$ is O or NH, and n is as defined above.

Further, the monomers of Formula (A1), optional (A2), (B1), (B2), and (B3) can be used in any ratio not inconsistent with the objectives of the present disclosure. In addition, altering the ratios of monomers can, in some embodiments, alter the antimicrobial properties, the biodegradability, the mechanical strength, and/or other properties of the polymer formed from the monomers. In some embodiments, the ratio of monomer (A1) to monomer (B1), monomer (B2), or monomer (B3) is between about 1:10 and about 10:1 or between about 1:5 and about 5:1. In some embodiments, the ratio of monomer (A1) to monomer (B1), monomer (B2), or monomer (B3) is between about 1:4 and about 4:1. In some embodiments, the ratio is about 1:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1. Additionally, when (A2) is reacted, the ratio of monomer (A2) to monomer (B1), monomer (B2), or monomer (B3), in some instances, is between about 1:10 and about 10:1 or between about 1:5 and about 5:1. In some embodiments, the ratio of monomer (A2) to monomer (B1), monomer (B2), or monomer (B2) is between about 1:4 and about 4:1. In some embodiments, the ratio is about 1:1.

In addition, in some embodiments, a polymer described herein comprises the reaction product of (i) an alkoxylated or alkenoxylated citric acid, citrate, or ester/amide of citric acid, and optionally, a non-alkoxylated and non-alkenoxylated citric acid, citrate, or ester/amide of citric acid with (ii) a polyol/polyamine, and (iii) a catechol-containing species. The alkoxylated or alkenoxylated citric acid, citrate, or ester/amide of citric acid can be an alkoxylated or alkenoxylated citric acid, citrate, or ester/amide of citric acid described above. Similarly, the polyol/polyamine can be any polyol/polyamine described above, which may in some cases be referred to herein as a biodegradable photoluminescent polymer (BPLP).

The catechol-containing species can comprise any catechol-containing species not inconsistent with the objectives of the present disclosure. In some cases, a catechol-containing species used to form an alkoxylated or alkenoxylated citrate-containing polymer described herein comprises at least one moiety that can form an ester or amide bond with another chemical species used to form the polymer. For example, in some cases, a catechol-containing species comprises an alcohol moiety, an amine moiety, a carboxylic acid moiety, or a combination thereof. Further, in some instances, a catechol-containing species comprises a hydroxyl moiety that is not part of the catechol moiety. In some embodiments, a catechol-containing species comprises dopamine. In other embodiments, a catechol-containing species comprises L-3,4-dihydroxyphenylalanine (L-DOPA) or D-3,4-dihydroxyphenylalanine (D-DOPA). In still other embodiments, a catechol-containing species comprises gallic acid or caffeic acid. In some cases, a catechol-containing species comprises 3,4-dihydroxyhydrocinnamic acid. Additionally, a catechol-containing species may also comprise a naturally-occurring species or a derivative thereof, such as tannic acid or a tannin. Moreover, in some embodiments, a catechol-containing species is coupled to the backbone of the polymer through an amide bond. In other embodiments, a catechol-containing species is coupled to the backbone of the polymer through an ester bond. In some embodiments, the catechol-containing species may be represented by Formula (C):

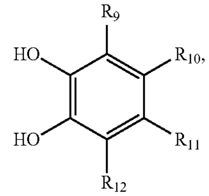

wherein $R_9$, $R_{10}$, $R_{11}$, and $R_{12}$ are each independently —H, —OH, —$CH_2(CH_2)_xNH_2$, —$CH_2(CHR_{13})NH_2$, —$CH_2(CH_2)_xOH$, —$CH_2(CHR_{13})OH$, —$CH_2(CH_2)_xCOOH$, or a point of attachment to a polymer chain;
$R_{13}$ is —COOH or —$(CH_2)_yCOOH$;
x is an integer ranging from 0 to 10; and
y is an integer ranging from 1 to 10.

In some cases, a monomer of Formula (C) comprises dopamine, L-DOPA, D-DOPA, gallic acid, caffeic acid, 3,4-dihydroxyhydrocinnamic acid, or tannic acid. Moreover, in some embodiments, a monomer of Formula (C) is coupled to the backbone of the polymer through an amide bond. In other embodiments, a monomer of Formula (C) is coupled to the backbone of the polymer through an ester bond.

Figure 10:
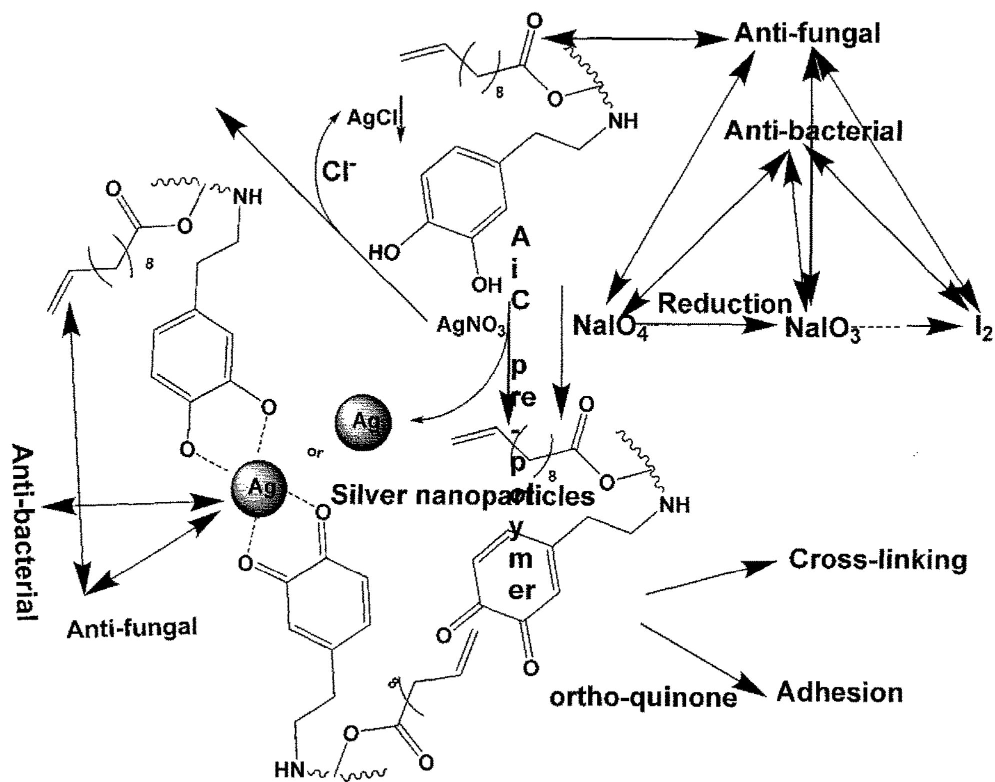
FIG. 10 illustrates functionalities of polymers or oligomers according to some embodiments described herein.

In some embodiments wherein a catechol containing species of Formula (C) is reacted, a cross-linking agent or initiator, or oxidant may be including in a composition described herein. In particular, such a species can be a cross-linking agent or initiator or an oxidant of the hydroxyl moieties of the catechol group of the species of Formula (C). Not intending to be bound by theory, it is believed that the catechol hydroxyl groups are oxidized by the oxidant to form an ortho-quinone. Formation of the ortho-quinone subsequently triggers intermolecular cross-linking of the herein-described polymer compositions. Exemplary oxidant cross-linking initiators that might be added include sodium periodate ($NaIO_4$) and/or silver nitrate ($AgNO_3$). However, other oxidants of the catechol hydroxyl groups may also be used. In some embodiments, some or all of these added oxidants are reduced, for example, to sodium iodate ($NaIO_3$) and iodine ($I_2$), or silver nanoparticles, respectively, in the case of sodium periodate ($NaIO_4$) and silver nitrate ($AgNO_3$). Moreover, it is to be understood that such oxidants and their reduction products (or "reduced oxidants") can themselves provide antimicrobial properties. For example, $NaIO_4$, $AgNO_3$, $NaIO_3$, $I_2$, and silver nanoparticles can be antibacterial, and/or antifungal agents. FIG. 10 shows possible oxidation-reduction reactions that might occur when $NaIO_4$ or $AgNO_3$ are added to a compositions, as described herein, that comprise a catechol containing species, e.g., one of Formula (C). As shown in FIG. 10, the hydroxyl groups of the catechol containing species can act as reducing agents, thereby initiating cross-linking. The hydroxyl groups can also be important for the adhesion of the compositions described herein to substrates. In some embodiments, $NaIO_4$ is preferably used, for example, as an oxidant cross-linking initiator, to provide cross-linked compositions with improved wet tissue adhesion strength.

In some embodiments, release of the foregoing small molecules or nanoparticulate oxidants and/or reduced oxidants from the above-described compositions provides a short-term antimicrobial activity. As described further below, these small molecule/nanoparticulate antibacterial and/or antifungal agents can be released over a shorter time period than, for example, other antibacterial and/or antifungal agents that can be released from compositions described herein. This short-term antimicrobial activity may a burst of activity and may be strong.

It is further to be understood that, in some embodiments, the above-described short-term antimicrobial activity may be observed in compositions that do not comprise one or more alkoxylated or alkenoxylated citrate-containing polymers or oligomers, but are instead formed a monomer of Formula (A2) and not from a monomer of Formula (A1). For example, in compositions formed by reacting a non-alkoxylated and non-alkenoxylated citric acid, citrate, or ester/amide of citric acid with (ii) a polyol/polyamine, and (iii) a catechol-containing species, short-term antimicrobial activity may result when oxidant cross-linking initiators such as sodium periodate ($NaIO_4$) and/or silver nitrate ($AgNO_3$) are added. Thus, a short-term burst of antimicrobial activity may occur in compositions where an alkoxylated or alkenoxylated citric acid, citrate, or ester/amide of citric acid are not reacted. Such antimicrobial compositions are also contemplated herein.

Any amount of oxidant (e.g., a sodium periodate ($NaIO_4$) and/or silver nitrate ($AgNO\text{-}_3$) oxidant cross-linking initiator) not inconsistent with the objectives of the present disclosure may be added to any of the herein-described polymer compositions. For example, amounts from 0.0001 to 5 wt. % of oxidant, based on the total weight of the composition, may be added. Amounts of 0.001 to 4 wt. %, 0.001 to 3 wt. %, 0.001 to 2 wt. %, 0.001 to 1 wt. %, or 0.001 to 0.5 wt. % may also be added in some cases. These amounts include total amounts of oxidant, e.g., amounts of $NaIO_4$, amounts of $AgNO_3$, or combined amounts of $NaIO_4$ and $AgNO_3$.

Further, in some embodiments, a monomer of Formula (B1), (B2), or (B3) can be replaced by an alcohol that does not have the formula of Formula (B1), (B2), or (B3). For example, in some embodiments, an unsaturated alcohol or an unsaturated polyol can be used. Moreover, the monomers of Formula (A1), optional (A2), (B1), (B2), (B3) and (C) can be used in any ratio not inconsistent with the objectives of the present disclosure. In addition, altering the ratios of monomers can, in some embodiments, alter the antimicrobial properties and/or other properties of the alkoxylated or alkenoxylated citrate-containing polymer formed from the monomers. In some embodiments, the ratio of monomer (A1) or monomer (A2) to monomer (B1), monomer (B2), or monomer (B3) is between about 1:10 and about 10:1 or between about 1:5 and about 5:1. In some embodiments, the ratio of monomer (A1) or monomer (A2) to monomer (B1), monomer (B2), or monomer (B3) is between about 1:4 and about 4:1. In some cases, the ratio is about 1:1. Further, in some embodiments, the ratio of monomer (A1) or monomer (A2) to monomer (C) is between about 1:10 and about 10:1. Further, in some embodiments, the ratio of monomer (A1) to monomer (A2) is between about 1:10 and about 10:1.

An alkoxylated or alkenoxylated citrate-containing polymer of a composition described herein, in some cases, can comprise the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine, and (iii) an alcohol/amine, an amide, carboxylic acid, or an isocyanate. In such instances, the polyol/polyamine can comprise any polyol/polyamine described above, and the ester/amine of citric acid can comprise any ester/amide of citric acid described above. Further, an amine, in some embodiments, comprises one or more primary amines having two to ten carbon atoms. In other cases, an amine comprises one or more secondary or tertiary amines having two to fifteen carbon atoms. An isocyanate, in some embodiments, comprises a monoisocyanate. In other instances, an isocyanate comprises a diisocyanate such as an alkane diisocyanate having four to twenty carbon atoms. An isocyanate described herein may also include a monocarboxylic acid moiety.

In some embodiments, the isocyanate may be represented by Formula (D1), Formula (D2), Formula (D3), and/or Formula (D4):

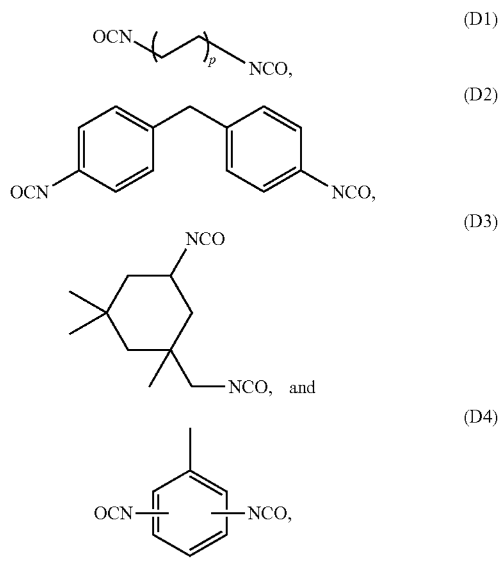

wherein p is an integer ranging from 1 to 10.

In addition, an alkoxylated or alkenoxylated citrate-containing polymer of a composition described herein can also comprise the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine, and (iii) a polycarboxylic acid such as a dicarboxylic acid or a functional equivalent of a polycarboxylic acid, such as a cyclic anhydride or an acid chloride of a polycarboxylic acid. In such cases, the polyol/polyamine can comprise any polyol/polyamine described above, and the ester of citric acid can comprise any ester/amide of citric acid described above. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. A vinyl-containing polycarboxylic acid or functional equivalent thereof may also be used, such as allylmalonic acid, allylmalonic chloride, itaconic acid, or itaconic chloride. Further, in some cases, the polycarboxylic acid or functional equivalent thereof can be at least partially replaced with an olefin-containing monomer that may or may not be a polycarboxylic acid. In some embodiments, for instance, an olefin-containing monomer comprises an unsaturated polyol such as a vinyl-containing diol.

In some embodiments, the polycarboxylic acid may be represented by Formula (E1) and/or Formula (E2):

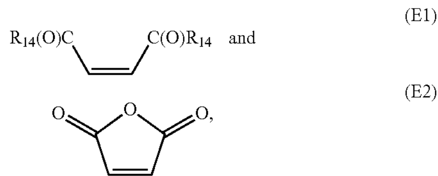

wherein $R_{14}$ is —OH, —$OCH_3$, —$OCH_2CH_3$, or —Cl.

Further, the monomers of Formula (A1), optional (A2), (B1), (B2), (E1) and (E2) can be used in any ratio not inconsistent with the objectives of the present disclosure. In addition, altering the ratios of monomers can, in some embodiments, alter the antimicrobial properties, the biodegradability, the mechanical strength, and/or other properties of the polymer formed from the monomers. In some embodiments, the ratio of monomer (A1) or monomer (A2) to monomer (B1), monomer (B2), or monomer (B3) is between about 1:10 and about 10:1 or between about 1:5 and about 5:1. In some embodiments, the ratio of monomer (A1) or monomer (A2) to monomer (B1), monomer (B2), or monomer (B3) is between about 1:4 and about 4:1. In some embodiments, the ratio is about 1:1. Further, in some embodiments, the ratio of monomer (A1) or monomer (A2) to monomer (E1) or monomer (E2) is between about 1:10 and about 10:1. In some embodiments, the ratio of monomer (A1) or monomer (A2) to monomer (E1) or monomer (E2) is about 1:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

In still other embodiments, an alkoxylated or alkenoxylated citrate-containing polymer described herein comprises the reaction product of (i) an alkoxylated or alkenoxylated citric acid, citrate, or ester/amide of citric acid, and optionally, a non-alkoxylated and non-alkenoxylated citric acid, citrate, or ester/amide of citric acid with (ii) a polyol/polyamine, and (iii) an amino acid such as an alpha-amino acid. An alpha-amino acid of a polymer described herein, in some embodiments, comprises an L-amino acid, a D-amino acid, or a D,L-amino acid. In some cases, an alpha-amino acid comprises alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan, valine, or a combination thereof. Further, in some instances, an alpha-amino acid comprises an alkyl-substituted alpha-amino acid, such as a methyl-substituted amino acid derived from any of the 22 “standard” or proteinogenic amino acids, such as methyl serine.

In some embodiments, an alkoxylated or alkenoxylated citrate-containing polymer of a composition described herein is formed from the following: one or more monomers of Formula (A1); optionally one or more monomers of Formula (A2); one or more monomers of Formula (B1), (B2), or (B3); and one or more amino acid monomers represented by Formula (F):

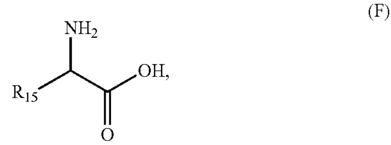

wherein $R_{15}$ is an amino acid side chain.

Moreover, the monomers of Formula (A1), optional (A2), (B1), (B2), (B3), and (F) can be used in any ratio not inconsistent with the objectives of the present disclosure. In addition, altering the ratios of monomers can, in some embodiments, alter the antimicrobial properties and/or other properties of the alkoxylated or alkenoxylated citrate-containing polymer formed from the monomers. In some embodiments, the ratio of monomer (A1) or monomer (A2), if reacted, to monomer (B1), monomer (B2), or monomer (B3) is between about 1:10 and about 10:1 or between about 1:5 and about 5:1. In some embodiments, the ratio of monomer (A1) or monomer (A2), if reacted, to monomer (B1), monomer (B2), or monomer (B3) is between about 1:4 and about 4:1. In some cases, the ratio is about 1:1. Further, in some embodiments, the ratio of monomer (A1), monomer (A2), monomer (B1), monomer (B2), or monomer (B3) to monomer (F) is between about 1:10 and about 10:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

A reaction product described hereinabove, in some cases, is a condensation polymerization reaction product of the identified species. Thus, in some embodiments, at least two of the identified species are comonomers for the formation of a copolymer. In some such embodiments, the reaction product forms an alternating copolymer or a statistical copolymer of the comonomers. Additionally, species described hereinabove may also form pendant groups or side chains of a copolymer, or may form cyclic structures that may form part of the backbone of the polymer. Moreover, in some cases, the amount or ratio of a comonomer or other reactant comprising an alkoxylated or alkenoxylated citrate moiety can be selected to provide a desired antimicrobial effect to the alkoxylated or alkenoxylated citrate-containing polymer. Surprisingly, it has been discovered that some antimicrobial properties of a composition described herein can be tuned by varying one or more of the mole percent or weight percent of an alkoxylated or alkenoxylated citrate moiety in an alkoxylated or alkenoxylated citrate-containing polymer, the biodegradability of an alkoxylated or alkenoxylated citrate-containing polymer, and the water swellability of an alkoxylated or alkenoxylated citrate-containing polymer. In some cases, an alkoxylated or alkenoxylated citrate-containing polymer described herein comprises at least about 30 mole percent, at least about 40 mole percent, or at least about 50 mole percent citrate moiety, based on the total number of moles of the comonomers of the polymer. In some embodiments, an alkoxylated or alkenoxylated citrate-containing polymer described herein comprises between about 30 mole percent and about 70 mole percent, between about 30 mole percent and about 60 mole percent, between about 30 mole percent and about 50 mole percent, between about 35 mole percent and about 60 mole percent, between about 35 mole percent and about 55 mole percent, between about 40 mole percent and about 70 mole percent, between about 40 mole percent and about 60 mole percent, or between about 40 mole percent and about 55 mole percent alkoxylated or alkenoxylated citrate moiety, based on the total number of moles of the comonomers of the polymer. Similarly, in some cases, an alkoxylated or alkenoxylated citrate-containing polymer described herein comprises at least about 5 weight percent, at least about 10 weight percent, or at least about 15 weight percent, at least about 25 weight percent, at least about 30 weight percent, or at least about 40 weight percent alkoxylated or alkenoxylated citrate moiety, based on the total weight of the polymer. In some embodiments, an alkoxylated or alkenoxylated citrate-containing polymer described herein comprises between about 5 weight percent and about 80 weight percent, between about 5 weight percent and about 70 weight percent, between about 10 weight percent and about 80 weight percent, between about 10 weight percent and about 60 weight percent, between about 20 weight percent and about 80 weight percent, between about 20 weight percent and about 60 weight percent, between about 30 weight percent and about 80 weight percent, or between about 40 weight percent and about 70 weight percent alkoxylated or alkenoxylated citrate moiety, based on the total weight of the polymer.

In general, an alkoxylated or alkenoxylated citrate-containing polymer described herein can be an alkoxylated or alkenoxylated derivative of a polymer or oligomer described in U.S. Pat. No. 7,923,486; U.S. Pat. No. 8,530,611; U.S. Pat. No. 8,574,311; U.S. Pat. No. 8,613,944; U.S. Patent Application Publication No. 2012/0322155; U.S. Patent Application Publication No. 2013/0217790; or U.S. Patent Application Publication No. 2014/066587; the entireties of which are hereby incorporated by reference. For example, in some cases, an alkoxylated or alkenoxylated citrate-containing polymer of a composition described herein comprises an alkoxylated or alkenoxylated poly(ethylene glycol maleate citrate) (PEGMC), poly(octamethylene citrate) (POC), poly (octamethylene maleate anhydride citrate) (POMC), or a crosslinkable urethane doped elastomer (CUPE) or biodegradable photoluminescent polymer (BPLP). As described above, it is to be understood that an alkoxylated or alkenoxylated derivative of a polymer or oligomer described above can be a variation of the polymer or oligomer above in which the citrate moiety of the polymer or oligomer is at least partially replaced by an alkoxylated or alkenoxylated citrate moiety, such as that of Formula (A) herein.

Further, one or more other properties of an alkoxylated or alkenoxylated citrate-containing polymer described herein may also be tuned based on the amount of the alkoxylated or alkenoxylated citrate moiety and/or on one or more other features of the chemical structure of the polymer. For example, in some cases, the water uptake and/or degradation rate of a polymer described herein can be tuned for a desired application. Such tunability can provide further advantages to a composition described herein. For example, as described above, some previous biodegradable polymers and gels require incorporation of antibiotics or inorganic materials like silver nanoparticles to exhibit antimicrobial properties. Thus, a high swelling ratio of such polymers could lead to a "burst" release rather than a sustained release of bacteria-killing and/or fungi-killing agents, thereby limiting the anti-infection applications of such compositions. In contrast, some alkoxylated or alkenoxylated citrate-containing polymers and compositions described herein can have decoupled swelling and antimicrobial properties. Therefore, the structure and chemical composition of some alkoxylated or alkenoxylated citrate-containing polymers and compositions described herein can be selected to satisfy other requirements, such as mechanical requirements, without the need to sacrifice antimicrobial performance, including long term antimicrobial performance.

Additionally, an alkoxylated or alkenoxylated citrate-containing polymer described herein can have at least one ester bond in the backbone of the polymer. In some cases, a polymer has a plurality of ester bonds in the backbone of the polymer, such as at least three ester bonds, at least four ester bonds, or at least five ester bonds. In some embodiments, a polymer described herein has between two ester bonds and fifty ester bonds in the backbone of the polymer. Polymers having one or more ester bonds in the backbone of the polymer can be hydrolyzed in a biological or other aqueous environment to release free citric acid or citrate, in addition to other components. Not intending to be bound by theory, it is believed that the presence of citric acid in a biological environment can contribute to pH reduction, which may depress the internal pH of bacteria and alter the permeability of the bacterial membrane by disrupting substrate transport.

Further, alkoxylated or alkenoxylated citrate-containing polymers having a structure described herein, in some cases, can be biodegradable. A biodegradable polymer, in some embodiments, degrades in vivo to non-toxic components which can be cleared from the body by ordinary biological processes. In some embodiments, a biodegradable polymer completely or substantially completely degrades in vivo over the course of about 90 days or less, about 60 days or less, or about 30 days or less, where the extent of degradation is based on percent mass loss of the biodegradable polymer, and wherein complete degradation corresponds to 100% mass loss. Specifically, the mass loss is calculated by comparing the initial weight ($W_0$) of the polymer with the weight measured at a pre-determined time point ($W_t$) (such as 30 days), as shown in equation (1):

$$\text{Mass loss } (\%) = \frac{(W_0 - W_t)}{W_0} \times 100. \tag{1}$$

In some cases, the polymer or oligomer having surprisingly strong underwater adhesive properties is formed from one or more monomers of Formula (A1), optionally one or more monomers of Formula (A2), one or more monomers of Formula (B1), (B2), or (B3), and dopamine. In other cases, the polymer or oligomer having surprisingly strong underwater adhesive properties is formed from one or more monomers of Formula (A1), optionally one or more monomers of Formula (A2), one or more monomers of Formula (B1), (B2) or (B3), L-DOPA, D-DOPA or gallic acid, and caffeic acid, 3,4-dihydroxyhydrocinnamic acid, or tannic acid.

In some instances, the polymer or oligomer is formed from one or more monomers comprising a diamine. In some embodiments, the diamine may be represented by the structure of Formula (G):

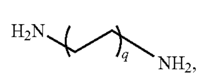

(G)

wherein q is an integer ranging from 1 to 20.

In some cases, the diamine may at least partially replace a diol monomer such as Formula (B1), Formula (B2), or Formula (B3) described hereinabove. In other cases, the diamine may be used in addition to diol monomers and/or instead of the diol monomers. Not intending to be bound by theory, the use of diamine will result in amide linkages in the polymer or oligomer, which may in turn result in slower degradation of the polymer or oligomer, giving a means to "tune" the degradability of the polymer or oligomer.

In some embodiments, the polymer or oligomer is formed from one or more monomers comprising one or more alkyne moieties or one or more azide moieties. In some cases, a composition described herein comprises the reaction product of (i) an alkoxylated or alkenoxylated citric acid, citrate, or ester of citric acid, and optionally, a non-alkoxylated and non-alkenoxylated citric acid, citrate, or ester/amide of citric acid, with (ii) a polyol such as a diol and (iii) a monomer comprising an alkyne moiety and/or an azide moiety. For example, in some cases, a composition described herein comprises a polymer formed from one or more monomers of Formula (A1); optionally one or more monomers of Formula (A2); one or more monomers of Formula (B1), (B2) or (B3); and one or more monomers comprising one or more alkyne moieties and/or one or more azide moieties. In some instances, the polymer is formed from monomers having a plurality of alkyne and/or azide moieties.

In addition, in some instances, a composition described herein comprises a plurality of polymers described herein, such as a first polymer formed from one or more monomers of Formula (A1); optionally one or more monomers of Formula (A2); one or more monomers of Formula (B1), (B2), or (B3); and one or more monomers comprising one or more alkyne moieties; and a second polymer formed from one or more monomers of Formula (A1); optionally one or more monomers of Formula (A2); one or more monomers of Formula (B1), (B2), or (B3); and one or more monomers comprising one or more azide moieties. Further, in some cases, a composition described herein comprises an azide-alkyne cycloaddition product, such as a 1,4-triazole ring or 1,5-triazole ring. Such a cycloaddition product can be formed from one or more polymers described herein. For example, in some cases, a first polymer and a second polymer of a composition described herein can form a polymer network by forming one or more azide-alkyne cycloaddition products from monomers comprising one or more alkyne moieties and one or more monomers comprising one or more azide moieties.

Further, monomers comprising one or more alkyne and/or azide moieties used to form a polymer described herein can comprise any alkyne- and/or azide-containing chemical species not inconsistent with the objectives of the present disclosure. For example, in some instances, one or more such monomers comprises a polyol/polyamine such as a diol/diamine. Such a monomer, in some cases, can be incorporated into the polymer through the reaction of one or more hydroxyl moieties of the monomer with a carboxyl or carboxylic acid moiety of a monomer of Formula (A1) or of another carboxyl-containing monomer described herein, e.g., an optional monomer of Formula (A2). Moreover, in some instances, such a monomer can be used instead of the monomer of Formula (B1), (B2), or (B3). In other instances, such a monomer is used in conjunction with one or more monomers of Formula (B1), (B2), or (B3). Further, such a monomer can be a diazido-diol (DAzD) or an alkyne diol (AlD).

In some cases, one or more monomers comprising one or more azide moieties comprises a monomer of Formula (H1), (H2), or (H3):

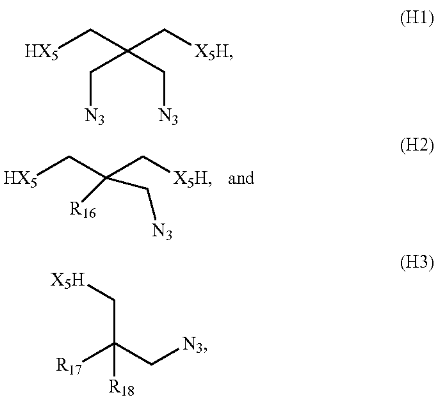

wherein $X_5$ is —O— or —NH—;

$R_{16}$ is $—CH_3$ or $—CH_2CH_3$; and $R_{17}$ and $R_{15}$ are each independently $—CH_2N_3$, $—CH_3$, or $—CH_2CH_3$.

Further, in some embodiments, one or more monomers comprising one or more alkyne moieties comprises a monomer of Formula (I1), (I2), (I3), (I4), (I5), or (I6):

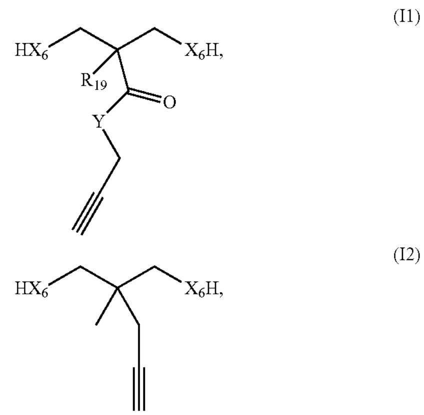

-continued

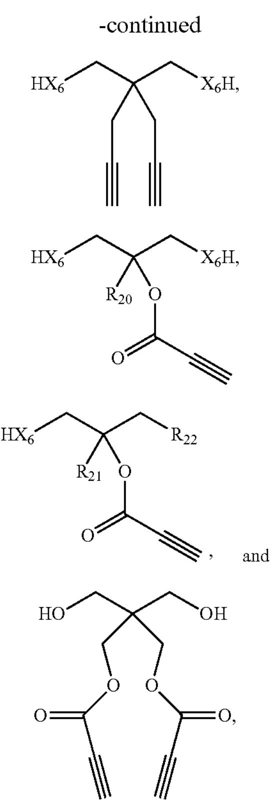

wherein $X_6$ and Y are each independently —O— or —NH—;

$R_{19}$ and $R_{20}$ are each independently $—CH_3$ or $—CH_2CH_3$;

$R_{21}$ is —O(CO)C≡CH, $—CH_3$, or $—CH_2CH_3$; and $R_{22}$ is $—CH_3$, —OH or $—NH_2$.

Additionally, in some embodiments, a polymer described herein can be functionalized with a bioactive species. In some cases, the polymer is formed from an additional monomer comprising the bioactive species. Moreover, such an additional monomer can comprise one or more alkyne and/or azide moieties. For example, in some instances, a polymer described herein is formed from one or more monomers comprising a peptide, polypeptide, nucleic acid, or polysaccharide, wherein the peptide, polypeptide, nucleic acid, or polysaccharide is functionalized with one or more alkyne and/or azide moieties. In some cases, the bioactive species of a polymer described herein is a growth factor or signaling molecule. Further, a peptide can comprise a dipeptide, tripeptide, tetrapeptide, or a longer peptide. As described further hereinbelow, forming a polymer from such a monomer, in some embodiments, can provide additional biological functionality to a composition described herein.

In addition, in some embodiments, a composition comprises a plurality of polymers described herein. In some instances, the polymers are selected to be reactive with one another through a click chemistry reaction scheme, as described above. In some cases, for example, a composition described herein comprises a first polymer formed from one or more monomers of Formula (A1); optionally one or more monomers of Formula (A2); one or more monomers of Formula (B1), (B2) or (B3); and one or more monomers comprising one or more alkyne moieties; and further comprises a second polymer formed from one or more monomers of Formula (A1); optionally one or more monomers of Formula (A2); one or more monomers of Formula (B1), (B2), or (B3); and one or more monomers comprising one or more azide moieties. Thus, in some such embodiments, a composition described herein can comprise an azide-alkyne cycloaddition product, such as a 1,4 or 1,5-triazole ring. In this manner, a first polymer and a second polymer of a composition described herein can form a polymer network by forming one or more azide-alkyne cycloaddition products to serve as cross-links of the polymer network. Other combinations of polymers are also possible.

A crosslinked polymer network described herein, such as a polymer network formed of click chemistry adducts, can have a high cross-linking density. "Cross-linking density," for reference purposes herein, can refer to the number of cross-links between polymer backbones or the molecular weight between cross-linking sites, calculated as described hereinbelow. Further, in some embodiments, the cross-links of a polymer network described herein comprise azide-alkyne cycloaddition product cross-links. Cross-links may also include ester bonds formed by the esterification or reaction of one or more pendant carboxyl or carboxylic acid groups with one or more pendant hydroxyl groups of adjacent polymer backbones. In some embodiments, a polymer network described herein has a cross-linking density of at least about 500, at least about 1000, at least about 5000, at least about 7000, at least about 10,000, at least about 20,000, or at least about 30,000 mol/$m^3$. In some cases, the cross-linking density is between about 5000 and about 40,000 or between about 10,000 and about 40,000 mol/$m^3$.

It is also possible to form a polymer network using a click chemistry reaction scheme that does not necessarily form azide-alkyne cycloaddition products. For instance, in some cases, one or more monomers comprising an alkyne and/or azide moiety described herein can be at least partially replaced by one or more monomers comprising a different moiety that can participate in a click chemistry reaction scheme. For example, in some embodiments, a polymer or polymer network is formed from the reaction of one or more monomers comprising a thiol moiety with one or more monomers comprising an alkene (or alkyne) moiety through a thiol-ene/yne click reaction. Such a thiol-ene/yne click reaction can comprise the addition of an S—H bond across a carbon-carbon double bond or triple bond by a free radical or ionic mechanism. More generally, in some cases, a polymer described herein can be formed from one or more monomers of Formula (A); one or more monomers of Formula (B1) or (B2); and one or more monomers comprising one or more first moieties operable to participate in a click chemistry reaction and/or one or more second moieties operable to participate in the same click chemistry reaction, where the first and second moieties differ. Any click chemistry reaction not inconsistent with the objectives of the present disclosure may be used. In some instances, the click chemistry reaction comprises a [3+2] cycloaddition such as a Huisgen alkyne-azide cycloaddition; a thiol-ene/yne reaction; a Diels-Alder reaction; an inverse electron demand Diels-Alder reaction; a [4+1] cycloaddition such as the cycloaddition reaction of an isocyanide with a tetrazine; or a nucleophilic substitution reaction involving a strained ring such as an epoxy or aziridine ring. Not intending to be bound by theory, it is believed that the use of a click chemistry reaction scheme to provide cross-linking in a polymer network can, in some cases, improve the mechanical strength of a polymer network without sacrificing pendant citric acid carboxyl moieties for other purposes, such as hydroxyapatite (HA) calcium chelation.

Moreover, in some instances, the polyol/polyamine above can be at least partially replaced by an alcohol having only one hydroxyl group or by an amine or an amide. Further, in some cases, the polyol/polyamine can be at least partially replaced by a polymer or oligomer having one or more hydroxyl, amine, or amide groups. Such a polymer or oligomer, in some instances, can be a polyester, polyether, or polyamide. Thus, in some embodiments, a composition described herein comprises the reaction product of (i) an alkoxylated or alkenoxylated citric acid, citrate, or ester/amide of citric acid with (ii) an alcohol, amine, amide, polyester, polyether, or polyamide and (iii) a monomer comprising an alkyne moiety and/or an azide moiety.

The monomers of Formula (A1), optional (A2), (B1), (B2), and (B3) and the monomers comprising one or more alkyne and/or azide moieties can be used in any ratio not inconsistent with the objectives of the present disclosure. In addition, altering the ratios of monomers can, in some embodiments, alter the biodegradability, the mechanical strength, and/or other properties of the polymer formed from the monomers. In some embodiments, the ratio of monomer (A1) or monomer (A2), if reacted, to monomer (B1), (B2), or (B3) is between about 1:10 and about 10:1 or between about 1:5 and about 5:1. In some embodiments, the ratio of monomer (A1) or monomer (A2), if reacted, to monomer (B1), (B2), or (B3) is between about 1:4 and about 4:1. In some embodiments, the ratio is about 1:1. The ratio of an alkyne or azide-containing monomer to a monomer of Formula (A1), optional (A2), (B1), or (B2) can be between about 1:20 and 1:2 or between about 1:10 and about 1:3.

A polymer network described herein can be prepared in any manner not inconsistent with the objectives of the present disclosure. In some cases, a method of making a polymer network comprises mixing and/or reacting a first polymer and a second polymer, the first and second polymer each comprising a polymer of a composition described herein. Moreover, the first and second polymers can comprise complementary functional groups for carrying out a cross-linking reaction, including through a click chemistry reaction scheme. For example, in some instances, the first polymer comprises one or more alkyne moieties, and the second polymer comprises one or more azide moieties. In some cases, the first polymer is formed from one or more monomers of Formula (A1); optionally one or more monomers of Formula (A2); one or more monomers of Formula (B1), (B2), or (B3); and one or more monomers comprising one or more alkyne moieties; and the second polymer is fainted from one or more monomers of Formula (A1); optionally one or more monomers of Formula (A2); one or more monomers of (B1), (B2), or (B3); and one or more monomers comprising one or more azide moieties. In such cases, the polymer network may be formed by reacting the one or more alkyne moieties of the first polymer with the one or more azide moieties of the second polymer to form one or more azide-alkyne cycloaddition products.

Reacting the alkyne and azide moieties can be carried out in any manner not inconsistent with the objectives of the present disclosure. In some embodiments, reacting the alkyne and azide moieties comprises heating the mixture of the first and second polymers to a temperature sufficient to induce a cross-linking reaction, such as a temperature of about 80° C. to about 120° C. to induce a thermal click chemistry reaction or an esterification reaction. Alkyne and azide moieties may also be reacted by providing a catalyst to the mixture, such as a metal catalyst. A metal catalyst suitable for use in some embodiments described herein can include one or more of copper, ruthenium, and silver. In other instances, a metal-containing catalyst such as a copper catalyst is not used. Further, reacting the alkyne and azide moieties of first and second polymers described herein can comprise inducing a click chemistry reaction between the azide and alkyne moieties. Such a click chemistry reaction can be a thermal click chemistry reaction or another type of click chemistry reaction, such as a strain promoted alkyne-azide cycloaddition (SPAAC) or a copper-catalyzed alkyne-azide cycloaddition (CuAAC). Moreover, carrying out a reaction between alkyne and azide moieties in a manner described herein can form a cross-linked polymer network, the cross-links of the network being formed by azide-alkyne cycloaddition reaction products such as 1,4- or 1,5-triazole rings. Additionally, in some embodiments, the first and/or second polymers can comprise one or more additional moieties that can form additional cross-links to provide a polymer network. For example, in some cases, the first polymer and/or the second polymer comprises one or more carboxylic acid groups and/or hydroxyl groups. In some such instances, additional cross-linking can occur through the formation of one or more ester bonds between the carboxylic acid and hydroxyl groups.

Moreover, in some embodiments, a method of making a polymer network described herein further comprises functionalizing the surface of the polymer network with one or more biofunctional species, such as one or more peptides, polypeptides, nucleic acids, and/or polysaccharides. Such functionalization can be carried out in any manner not inconsistent with the objectives of the present disclosure. For example, in some instances, a method described herein further comprises reacting one or more of a peptide, polypeptide, nucleic acid, and polysaccharide with a pendant alkyne and/or azide moiety on the cross-linked polymer network to provide a covalent bond between the cross-linked polymer network and the peptide, polypeptide, nucleic acid, and/or polysaccharide. In some cases, the peptide, polypeptide, nucleic acid, and/or polysaccharide comprises an alkyne or azide moiety, and formation of a covalent bond is carried out by inducing a further click chemistry reaction, such as a strain-promoted alkyne-azide cycloaddition reaction, between one or more alkyne and/or azide moieties of the polymer network and one or more alkyne and/or azide moieties of the peptide, polypeptide, nucleic acid, and/or polysaccharide. Such a reaction, in some instances, can be carried out at 37° C. in an aqueous environment. Additionally, a peptide, polypeptide, or other biofunctional species can be modified to be clickable by reacting the peptide, polypeptide, or other species with a reagent such as a Click-Easy® BCN N-hydroxysuccinimide ester, commercially available from Berry & Associates.

A composition, therefore, can comprise, consist, or consist essentially of a polymer or oligomer formed from the reaction product of (i) an alkoxylated or alkenoxylated citric acid, citrate, or ester/amide of citric acid, and optionally, a non-alkoxylated and non-alkenoxylated citric acid, citrate, or ester/amide of citric acid, with (ii) a polyol/polyamine such as a diol/diamine and one or more monomers of (iii) a catechol-containing species; an alcohol/amine, an amide, a carboxyl acid, or an isocyanate; a polycarboxylic acid such as a dicarboxylic acid or a functional equivalent of a polycarboxylic acid; an amino acid such as an alpha-amino acid; a diamine; and/or a monomer comprising an alkyne moiety and/or an azide moiety.

As described hereinabove, compositions described herein can provide antibacterial and/or antifungal activity even without the use or inclusion of antibiotic and/or antifungal agents other than the polymer or oligomer of the compositions. However, if desired, it is also possible to include such additional antibiotic and/or antifungal agents in a composition described herein. For example, in some cases, a composition described herein further comprises a drug dispersed in the polymer or oligomer. Such drugs may include, but are not limited to, antibiotics, antifungals, antimicrobial peptides, and/or antimicrobial inorganic compositions such as metal particles. Antibiotics can include bactericidal materials such as penicillins, cephalosporins, polymyxins, rifamycins, lipiarmycins, quinolones, and sulfonamides. Antibiotics can also include bacteriostatic materials such as macrolides, lincosamides and tetracyclines or cyclic lipopeptides, glycylcyclines, oxazolidinones, and lipiarmycins. Antifungals can include fungicidal materials such as amphotericin B, azole antifungals, echinocandins, or flucytosine.

Moreover, in some embodiments, a composition described herein comprising a polymer network can further comprise a particulate material dispersed in the polymer network. Any particulate material not inconsistent with the objectives of the present disclosure may be used. In some cases, the particulate material comprises one or more of hydroxyapatite, tricalcium phosphate, biphasic calcium phosphate, bioglass, ceramic, magnesium powder, magnesium oxide, magnesium alloy, and decellularized bone tissue particles. Other particulate materials may also be used, such as silver nanoparticles.

In addition, a particulate material described herein can have any particle size and/or particle shape not inconsistent with the objectives of the present disclosure. In some embodiments, for instance, a particulate material has an average particle size in at least one dimension of less than about 1000 μm, less than about 800 μm, less than about 500 μm, less than about 300 μm, less than about 100 μm, less than about 50 μm, less than about 30 μm, or less than about 10 μm. In some cases, a particulate material has an average particle size in at least one dimension of less than about 1 μm, less than about 500 nm, less than about 300 nm, less than about 100 nm, less than about 50 nm, or less than about 30 nm. In some instances, a particulate material has an average particle size recited herein in two dimensions or three dimensions. Moreover, a particulate material can be formed of substantially spherical particles, plate-like particles, needle-like particles, or a combination thereof. Particulate materials having other shapes may also be used.

A particulate material can be present in a composition described herein in any amount not inconsistent with the objectives of the present disclosure. For example, in some cases, a composition comprises up to about 70 weight percent, up to about 60 weight percent, up to about 50 weight percent, up to about 40 weight percent, or up to about 30 weight percent particulate material, based on the total weight of the composition. In some instances, a composition comprises between about 1 and about 70 weight percent, between about 10 and about 70 weight percent, between about 15 and about 60 weight percent, between about 25 and about 65 weight percent, between about 25 and about 50 weight percent, between about 30 and about 70 weight percent, between about 30 and about 50 weight percent, between about 40 and about 70 weight percent, or between about 50 and about 70 weight percent, based on the total weight of the composition. For example, in some cases, a composition comprising a polymer network described herein comprises up to about 65 weight percent hydroxyapatite.

Moreover, in some embodiments, a composition described herein can comprise a high amount of particulate material, such as an amount up to about 70 weight percent, even when the polymers used to form the polymer network have a low weight average molecular weight, such as a weight average molecular weight of less than about 2000, less than about 1000, or less than about 500. For example, in some instances, a composition described herein comprises a polymer network formed from a polymer described herein having a weight average molecular weight of less than about 2000, less than about 1000, or less than about 500, and further comprises hydroxyapatite particles dispersed in the polymer network in an amount up to about 70 weight percent. Additionally, in some cases, the polymer network is not cross-linked or substantially cross-linked, other than by any cross-linking that may be provided by the hydroxyapatite particles.

Further, a particulate material described herein can be dispersed in a polymer network in any manner not inconsistent with the objectives of the present disclosure. In some embodiments, for instance, the particulate material is mixed or ground into the polymer network. In addition, a particulate material described herein, in some cases, can be chelated or otherwise bound by one or more pendant functional groups of the polymer network. For instance, in some cases, a composition comprises hydroxyapatite particles dispersed in a polymer network described herein, wherein the hydroxyapatite is chelated by one or more pendant functional groups of the polymer network. In some embodiments, one or more carboxyl moieties or one or more citrate moieties of the polymer network chelate one or more calcium-containing portions of the hydroxyapatite.

Various components of compositions have been described herein. It is to be understood that a composition according to the present disclosure can comprise any combination of components and features not inconsistent with the objectives of the present disclosure. For example, in some cases, a composition described herein can comprise a combination, mixture, or blend of alkoxylated or alkenoxylated citrate-containing polymers described herein. Additionally, in some embodiments, such a combination, mixture, or blend can be selected to provide a composition having any antimicrobial property, biodegradability, mechanical property, and/or chemical functionality described herein.

Further, one or more alkoxylated or alkenoxylated citrate-containing polymers can be present in a composition described herein in any amount not inconsistent with the objectives of the present disclosure. In some cases, a composition consists or consists essentially of the one or more alkoxylated or alkenoxylated citrate-containing polymers. In other instances, a composition comprises up to about 95 weight percent, up to about 90 weight percent, up to about 80 weight percent, up to about 70 weight percent, up to about 60 weight percent, up to about 50 percent, or up to about 40 weight percent alkoxylated or alkenoxylated citrate-containing polymer, based on the total weight of the composition. In some embodiments, the balance of a composition described herein can be water or an aqueous solution.

Alkoxylated or alkenoxylated citrate-containing polymers of a composition described herein can be prepared in any manner not inconsistent with the objectives of the present disclosure. In some cases, for instance, an alkoxylated or alkenoxylated citrate-containing polymer described herein is prepared by one or more polycondensation reactions. Further, in some embodiments, a polycondensation reaction can be followed by cross-linking of the polymer. As described further herein, such cross linking can be thermal cross linking or photoinitiated cross linking such as ultraviolet (UV) cross-linking.

Various components of compositions have been described herein. It is to be understood that a composition according to the present disclosure can comprise any combination of components and features not inconsistent with the objectives of the present disclosure. Additionally, in some embodiments, such a combination can be selected to provide a composition having any biodegradability, mechanical property, and/or chemical functionality described herein.

II. Methods of Treating Microbial Infections

In another aspect, methods of treating microbial infections are described herein. In some embodiments, a method of treating a microbial infection comprises disposing a composition comprising an alkoxylated or alkenoxylated (or non-alkoxylated and non-alkenoxylated) citrate-containing polymer in an environment. In some cases, the environment is a biological environment. Any composition consistent with the above discussion Section I can be used. The composition can be disposed in or on any biological environment not inconsistent with the present invention. For example, the biological environment can be in vivo or in vitro. In some embodiments, the biological environment is in or on a living patient. In some embodiments, a biological environment a surface of skin of a living patient. A wound or lesion may be present on the surface of skin, and thus, in some cases, disposing the composition on the surface of skin can comprise disposing the composition on or in a wound or lesion. In other cases, a biological environment comprises a tissue growth or regeneration region. In some instances, a biological environment comprises bone. Similarly, in some embodiments, the biological environment is a diabetic ulcer of a living patient.

Methods described herein can be used to treat various types of infections. For example, in some embodiments, the infection to be treated is a bacterial infection or a fungal infection. Further, in some embodiments, the microbial infection comprises both a bacterial infection and a fungal infection. Treating a microbial infection can comprise or include killing bacteria and/or fungi. Alternatively and/or additionally, treating a microbial infection can comprise or include reduction of microbial proliferation.

In some cases, the method comprises killing at least about 10% of the bacteria and at least 10% of the fungi, at least about 30% of the bacteria and at least 30% of the fungi, or at least 50% of the bacteria and 50% of the fungi. Additional ranges of bacteria and/or fungi killed in certain embodiments are provided herein below in Table 1.

TABLE 1

| Bacteria Killed (%) | Fungi Killed (%) |
|---|---|
| 10-99 | 10-99 |
| 10-90 | 10-90 |
| 10-80 | 10-80 |
| 10-70 | 10-70 |
| 10-50 | 10-50 |
| 20-99 | 20-99 |
| 30-99 | 30-99 |
| 50-99 | 50-99 |
| 20-90 | 20-90 |
| 20-80 | 20-80 |

Moreover, in some cases, a percentage of bacteria and/or fungi described herein is killed over the course of at least about 2 hours, at least about 4 hours, at least about 6 hours, at least about 8 hours, at least about 12 hours, at least about 18 hours, or at least about 24 hours. In some embodiments, a percentage of bacteria and/or fungi described herein is killed over the course of about 4 to 28 hours following disposing the composition in the biological environment. Thus, in some cases, a method of treating a bacterial and/or fungal infection described herein can provide sustained bacteria and/or fungal death, rather than killing bacteria and/or fungi only during a short initial burst following the beginning of treatment.

Moreover, in some instances, a method of treating a bacterial and/or fungal infection described herein can provide sustained bacterial and/or fungal death as described above over a time period ($t_1$) in addition to providing a short initial burst of bacterial and/or fungal death, following the beginning of treatment, over a time period ($t_2$). Thus, in some embodiments, ($t_2$) is a shorter time period than ($t_1$). However, it is to be understood that ($t_2$) and ($t_1$) can partially or completely overlap with one another. For example, in some instances, the short initial burst of bacterial and/or fungal death may occur seconds, minutes, or hours after the beginning of treatment. It may occur 1 second after the beginning of treatment or up to about 8 hours after the beginning of treatment. In some embodiments, it may occur 1 minute to 1 hour, 10 minutes to 3 hours, or 30 minutes to 5 hours after the beginning of treatment. Not intending to be bound by theory, it is believed that, in some embodiments, this short initial burst of bacterial and/or fungal death is caused by the release of certain "short term" or "burst release" antibacterials and/or antifungals from the composition. For example, in some embodiments, the short initial burst of bacterial and/or fungal death is caused by the release of an oxidant of a catechol group described herein and/or by the release of a reduced oxidant of the catechol group, where a "reduced oxidant" is understood to refer to the reduced species or "version" of the oxidant that results from the oxidation of the catechol group by the oxidant. For instance, in some embodiments, an oxidant used to oxidize catechol hydroxyl groups is sodium periodate ($NaIO_4$) or silver nitrate ($AgNO_3$), and the "reduced oxidant" is, respectively, sodium iodate ($NaIO_3$) or silver metal (Ag). Moreover, in some instances, the silver metal can be in the form of silver nanoparticles. Thus, in some cases, a short initial burst of bacterial and/or fungal death is caused by $NaIO_4$, $AgNO_3$, $NaIO_3$, $I_2$, and/or silver nanoparticles from the herein described compositions.

The "long term" release or antimicrobial activity of a method described herein, associated with the time period ($t_1$), can begin at the same time as the time period (t2), during ($t_2$), or after ($t_2$) is complete. Moreover, the long term time period ($t_1$) can be up to 2 weeks, up to 1 week, up to 5 days, up to 3 days, or up to 1 day. In some instances, the time period ($t_1$) is 12 hours to 2 weeks, 12 hours to 1 week, 12 hours to 5 days, 12 hours to 3 days, 1 day to 2 weeks, 1 day to 1 week, 1 to 5 days, 1 to 3 days, 3 days to 2 weeks, 3 days to 1 week, or 3 to 5 days. Additionally, not intending to be bound by theory, it is believed that "long term" antimicrobial activity can be caused by degradation of the polymer or oligomer of the composition, such that components of the polymer or oligomer (such as an alkoxylated or alkenyoxylated citrate-containing moiety, or a non-alkoxylated and non-alkenoxylated citrate-containing moiety) are released into the environment.

Thus, a method of treating a microbial infection described herein, in some embodiments, further comprises releasing an oxidant and/or reduced oxidant species described herein into the environment. A method described herein may also comprise at least partially degrading the alkoxylated or alkenoxylated citrate-containing polymer to release citric acid or a citrate into the environment, where the citric acid or citrate is alkoxylated or alkenoxylated or non-alkoxylated and non-alkenoxylated. At least partially degrading a polymer, in some cases, comprises cleaving one or more chemical bonds such as one or more ester bonds in the polymer, including in the polymer backbone. Further, in some instances, as described above, degrading an alkoxylated or alkenoxylated citrate-containing polymer in a manner described herein can provide a sustained release profile of citric acid. Moreover, releasing an oxidant and/or reduced oxidant species into the environment can be carried out before or at the same time as degrading the citrate-containing polymer, including in a manner consistent with time periods ($t_1$) and ($t_2$) described above.

Additionally, in some embodiments, microbial proliferation reduced by a method described herein comprises bacterial proliferation and/or fungal proliferation. In some cases, microbial proliferation in an environment described herein is reduced by at least about 10% compared to a negative control. In some embodiments, microbial proliferation in the environment is reduced by at least about 30%, at least about 50%, or at least about 70% compared to a negative control. In some cases, microbial proliferation in the environment is reduced by 10-80%, 10-70%, 10-60%, 20-80%, 20-60%, 20-50%, 20-40%, 30-80%, 30-70%, 30-60%, 40-80%, 40-70%, or 40-60%, compared to a negative control.

Some embodiments described herein are further illustrated in the following non-limiting examples.

EXAMPLE 1

Anti-Fungal Citric Acid Monomer (U-CA) Synthesis

A new anti-fungal citric acid monomer (which may also be referred to as an alkenoxylated citric acid monomer) designated as U-CA was synthesized by modifying citric acid (CA) with 10-undecylenic acid (UA) as shown in FIG. 1A. Citric acid (9.606 g, 0.05 mol) and zinc chloride ($ZnCl_2$, 0.6815 g, 0.005 mol, 0.1 eq. to CA) were added into 10-undecenoyl chloride (21.5 mL, 0.1 mol) in a dried 100-mL round-bottom flask. The reaction mixture was heated at 90° C. with stirring for 24 hrs. After cooling the reaction mixture to room temperature, diethyl ether (100 mL) was added to the mixture, and the resulting solution was poured into ice water (50 mL) with stirring. The organic portion was separated, dried over anhydrous sodium sulfate, and then the solvent was then evaporated. The crude product was purified by precipitation in hexane (250 mL). The product, an alkylene ester of citric acid, specifically, 10-undecylenic acid modified citric acid (U-CA), was obtained as viscous dark brown oil (12.7 g, 71% yield). $^1$H NMR (300 MHz; DMSO-d6; δ, ppm) of U-CA: 1.25-1.35 (s, $OCOCH_2CH_2$—$(CH_2)_5$— from UA), 1.52 (s, $OCOCH_2CH_2$— from UA), 1.98-2.05 (m, $CH_2$=CH—$CH_2$— from UA), 2.25-2.30 (m, $OCOCH_2$— from UA), 2.65-3.00 (m, —$CH_2$— from CA), 4.91-5.02 (m, $CH_2$=CH— from UA), 5.74-5.84 (m, $CH_2$=CH— from UA). FTIR of U-CA (cast film on KBr, $cm^{-1}$): 1897 (—$\underline{CH_2}$—) and 1733 ($\underline{CO}$OR).

EXAMPLE 2

U-CA and CA Pre Polymer Synthesis and Characterization

Figure 1B:
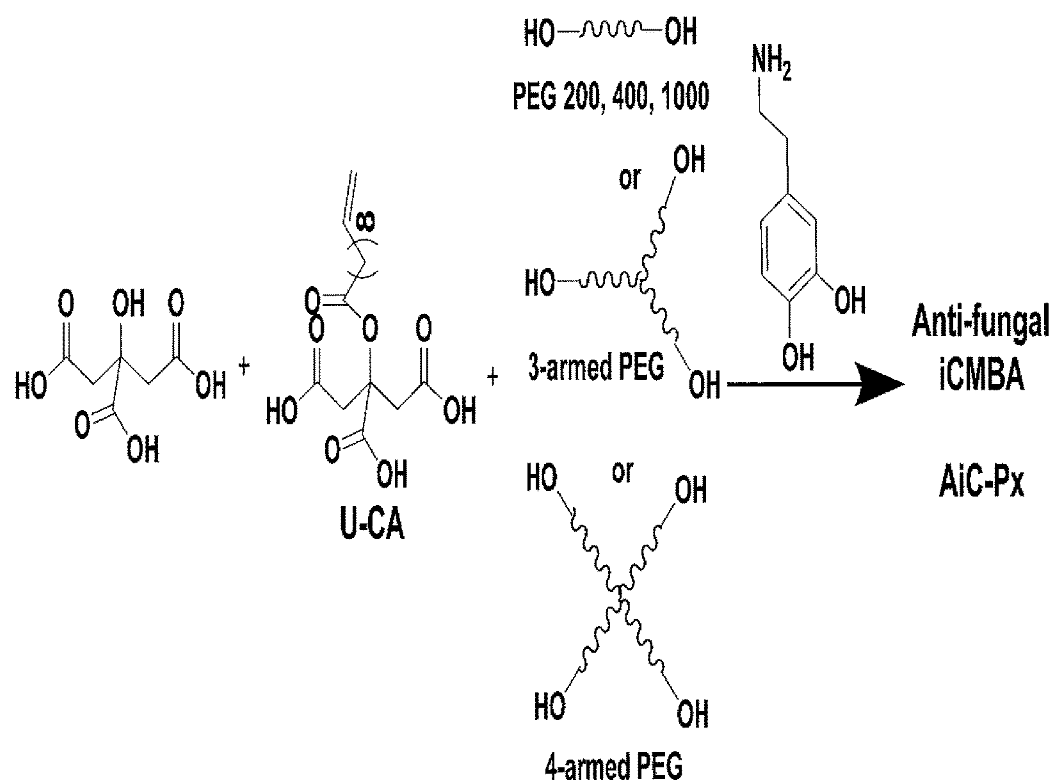

Anti-fungal injectable citrate-based mussel-inspired bioadhesive prepolymers, designated iCMBA (AiC), were synthesized by polycondensation of citric acid (CA), U-CA, poly(ethylene glycol) (PEG), and catechol-containing compounds, such as dopamine and L-DOPA (L-3,4-dihydroxyphenylalanine), as illustrated in FIG. 1B. Briefly, CA (17.29 g, 0.09 mol), U-CA (7.18 g, 0.02 mol) and PEG200 (with an average molecular weight of 200 Da, 20 g, 0.10 mol) were placed in a 100-mL round-bottom flask, and heated to 160° C. and stirred until a molten, clear mixture was formed. The temperature was reduced to 140° C., followed by the addition of dopamine (5.69 g, 0.03 mol) under $N_2$ atmosphere. The reaction was continued under vacuum for approximately 6 hrs until the viscosity of the solution prevented free movement of the stir bar at 60 rpm. The reaction was stopped and the pre-polymer was dissolved in deionized (DI) water and purified by extensive dialysis using a dialysis tube with a molecular weight cut-off (MWCO) of 500 Da. After freeze-drying of the dialyzed solution, a pre-polymer designated AiC-$P_{200}D_{0.3}$ was obtained. By adjusting the molecular weight and architectural structure (linear or branched) of PEG used, different AiC pre-polymers were synthesized as shown in Table 2. The feeding amount of dopamine was fixed at the ratio of 1.1/0.3 ((CA+U-CA)/dopamine). The polymers were named as follows. First, each polymer name includes either "iC" to designate normal injectable citrate-based mussel-inspired bioadhesives (iCMBAs) prepolymers that did not incorporate U-CA, or as "AiC" for anti-fungal iCMBA prepolymers that were formed using U-CA. This portion of the polymer names is then followed by a "P" and the molecular weight of the PEG (for example, $P_{200}$ is PEG 200 Da); and then by a "D" and the mole fraction of dopamine (for example, $D_{0.3}$ for a dopamine mole fraction of 0.3).

TABLE 2

Nomenclature, feeding ratio and dopamine content of pre-polymers.

| Pre-polymer name | Mw of PEG used (Da) | Feeding ratio of CA:U-CA:PEG:dopamine | Dopamine content in pre-polymer (mmol/g) |
|---|---|---|---|
| iC-$P_{200}D_{0.3}$ | 200 | 1.1:0:1:0.3 | 0.756 |
| AiC-$P_{200}D_{0.3}$ | 200 | 0.9:0.2:1:0.3 | 0.669 |
| AiC-$P_{400}D_{0.3}$ | 400 | 0.8:0.3:1:0.3 | 0.470 |
| AiC-$P_{2/4\ (1/1)}$ $D_{0.3}$ (PEG 200 and 400, w/w = 1/1) | 200 and 400 | 0.8:0.3:1:0.3 | 0.538 |
| AiC-$P_{1000}D_{0.3}$ | 1000 | 0.8:0.3:1:0.3 | 0.273 |
| AiC-P3$A_{1000}D_{0.3}$ | 1000 (3 armed) | 0.8:0.3:0.667:0.3 | 0.225 |
| AiC-P4$A_{800}D_{0.3}$ | 797 (4 armed) | 0.8:0.3:0.5:0.3 | 0.258 |

Figure 2A:
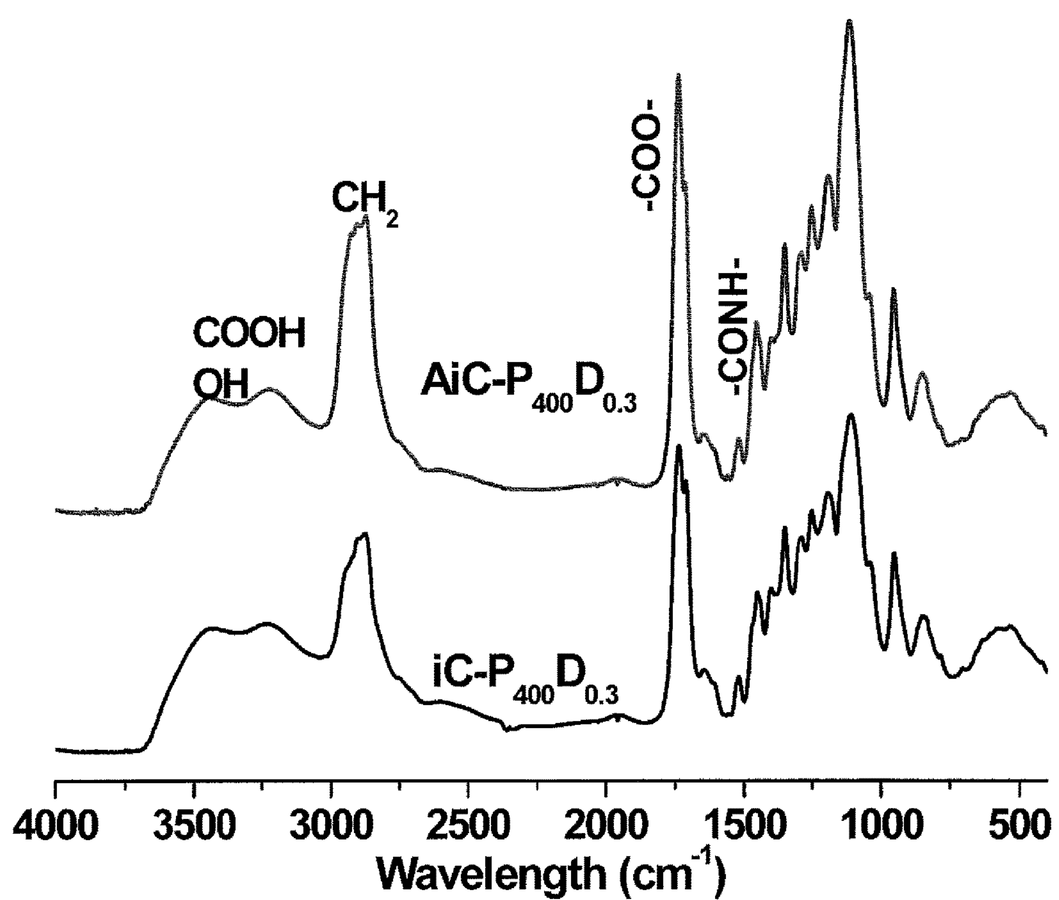
FIGS. 2A, 2B, 2C, and 2D each illustrate physical characterization of alkoxylated or alkenoxylated citrate-containing polymers according to some embodiments described herein.
Figure 2B:
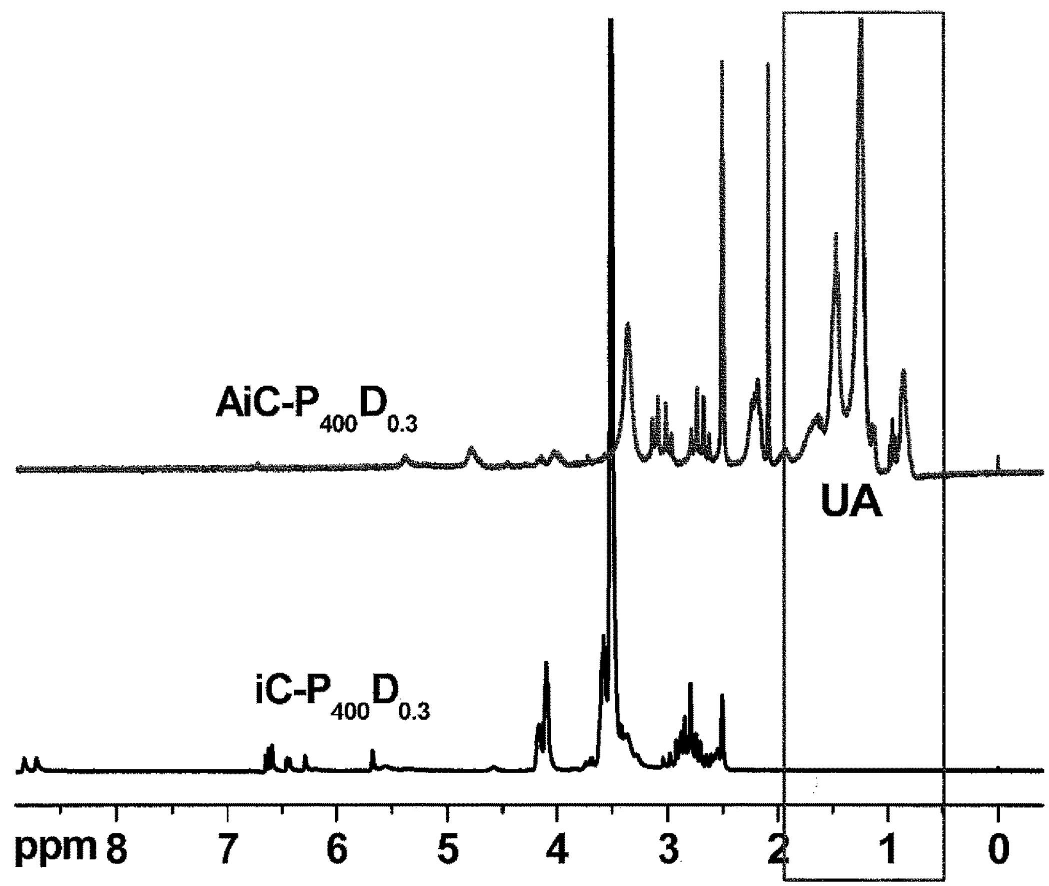
Figure 2C:
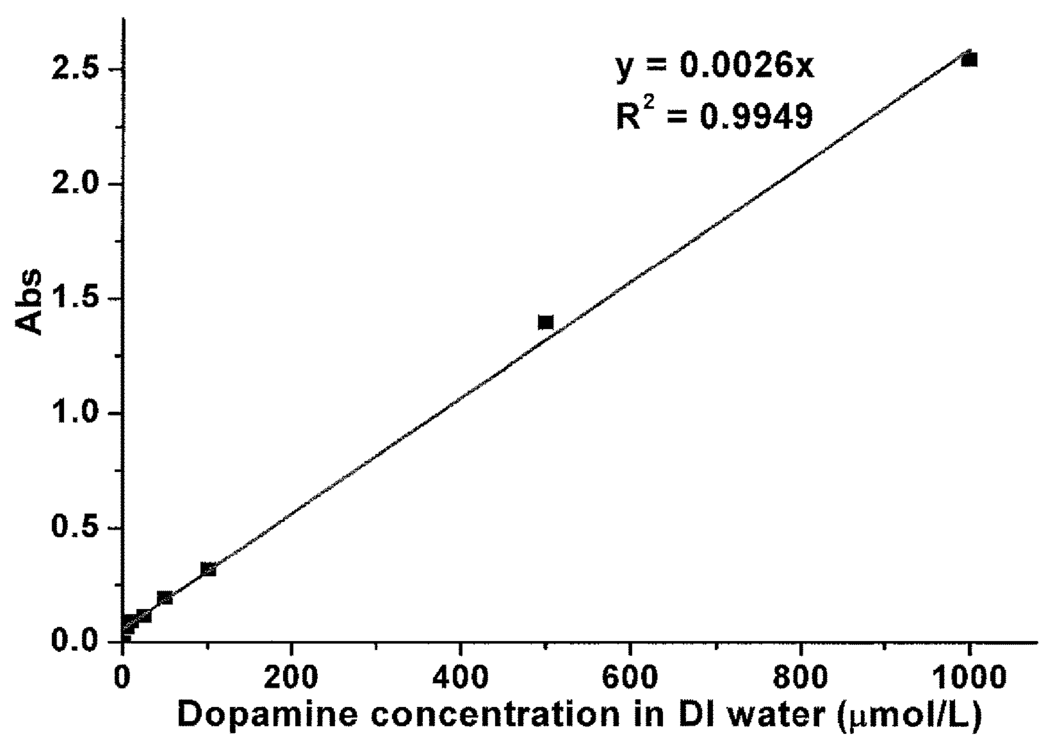
Figure 2D:
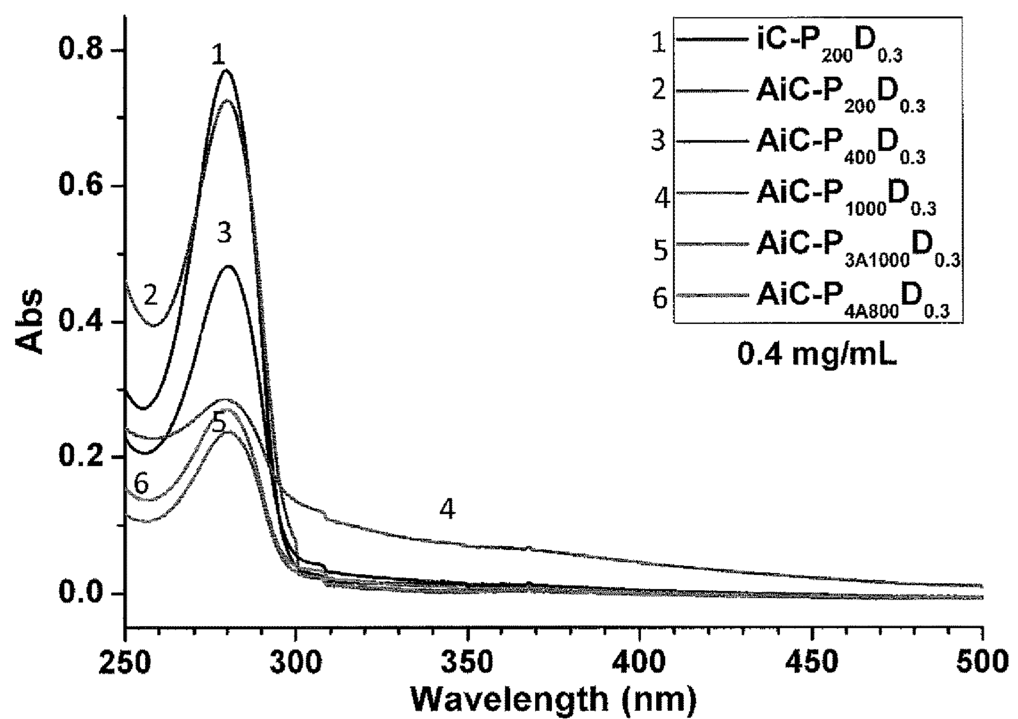

As shown in FIG. 2A, FTIR of iCMBA (iC-$P_{400}D_{0.3}$) and anti-fungal iCMBA (AiC-$P_{400}D_{0.3}$) were obtained (after casting polymer solution in acetone on KBr, $cm^{-1}$): 1898 (—$\underline{CH_2}$—) and 1734 ($\underline{COO}$—), 1633 ($\underline{CONH}$—). Representative $^1$H NMR (300 MHz; DMSO-d6; δ, ppm) spectra, as shown in FIG. 2B, of AiC pre-polymer: 1.22 (s, $OCOCH_2CH_2$—$(CH_2)_5$— from UA), 1.47 (s, $OCOCH_2CH_2$— from UA), 1.65 (m, $CH_2$=CH—$CH_2$— from UA), 2.25-2.30 (m, $OCOCH_2$— from UA), 2.65, 3.05 (m, —$CH_2$— from CA and citric acid of U-CA), 4.77 (broad, $CH_2$=CH— from UA), 5.34 (broad, $CH_2$=CH— from UA). As shown in FIG. 2C, the dopamine content in AiCs was also determined by UV-vis spectra, where absorbance of 0.4 mg/mL solution of various pre-polymers in DI water were measured using Shimadzu UV-2450 spectrophotometer across the wavelength of 700-200 nm. FIG. 2D depicts UV-vis absorption spectra of iCMBA and antiiCMBA pre-polymers in deionized water (with a pre-polymer concentration of 0.4 mg/mL).

EXAMPLE 3

Cross-Linking of AiC and Setting Time Measurement

Two different kinds of oxidants, silver nitrate ($AgNO_3$, SN for short) and sodium (meta) periodate (PI), were used to cross-link AiC into anti-bacterial and anti-fungal iCMBAs, designated AbAf iCs.

Figure 3A:
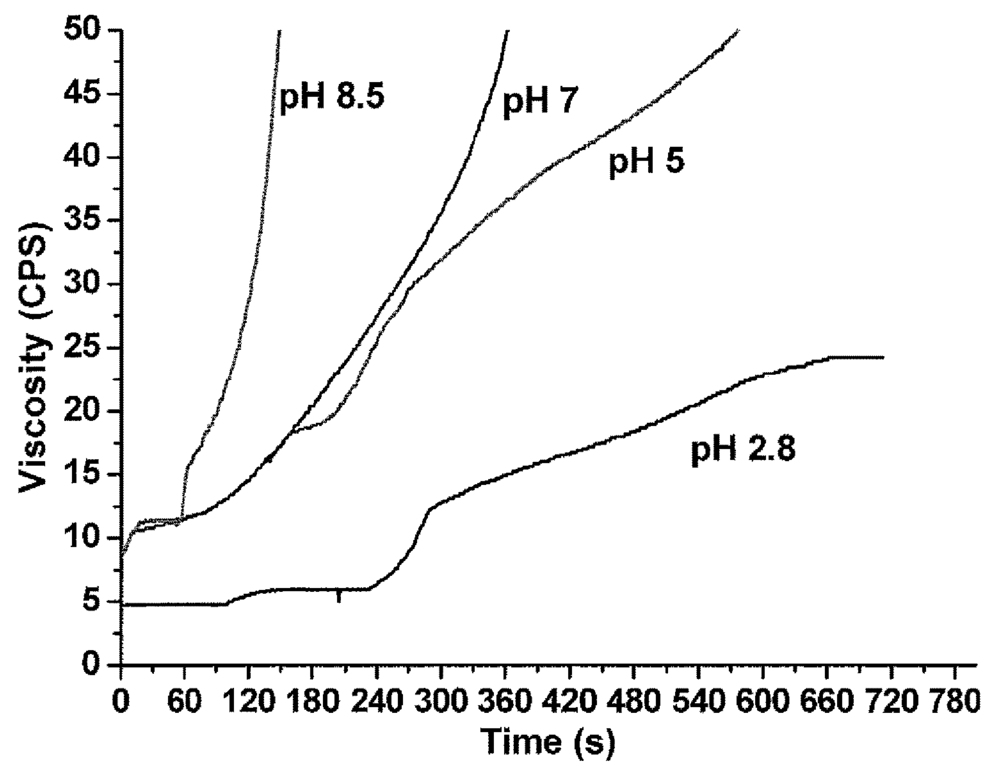
FIGS. 3A and 3B each illustrate plots of gelling properties of alkoxylated or alkenoxylated citrate-containing polymers according to some embodiments described herein.
Figure 3B:
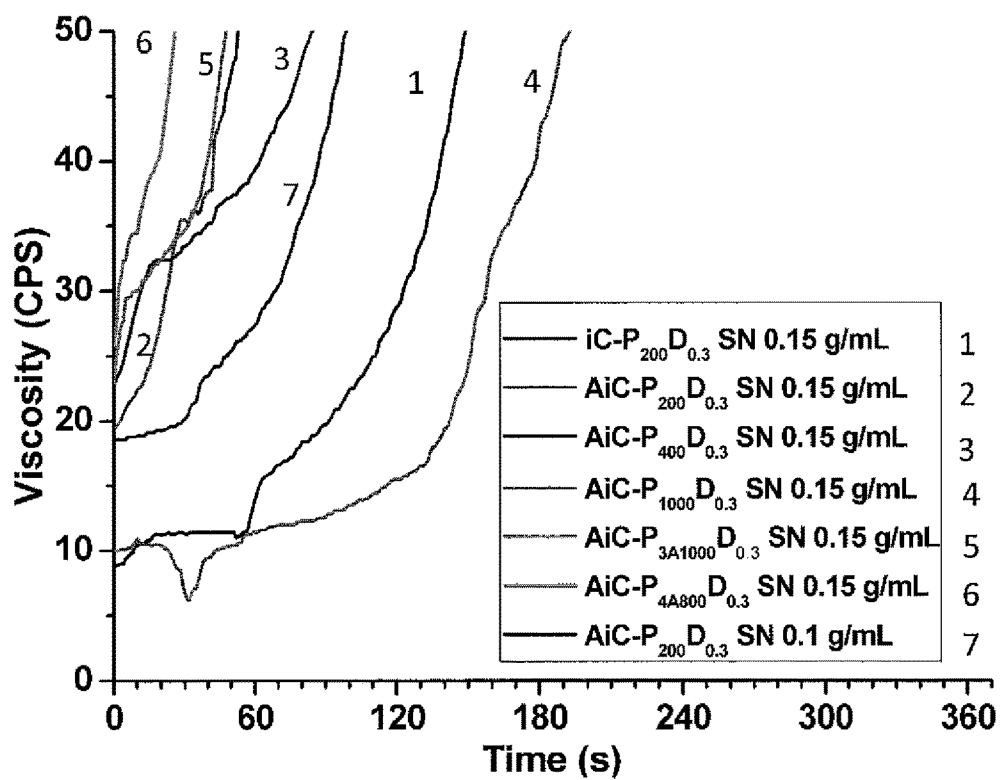
Figure 4A:
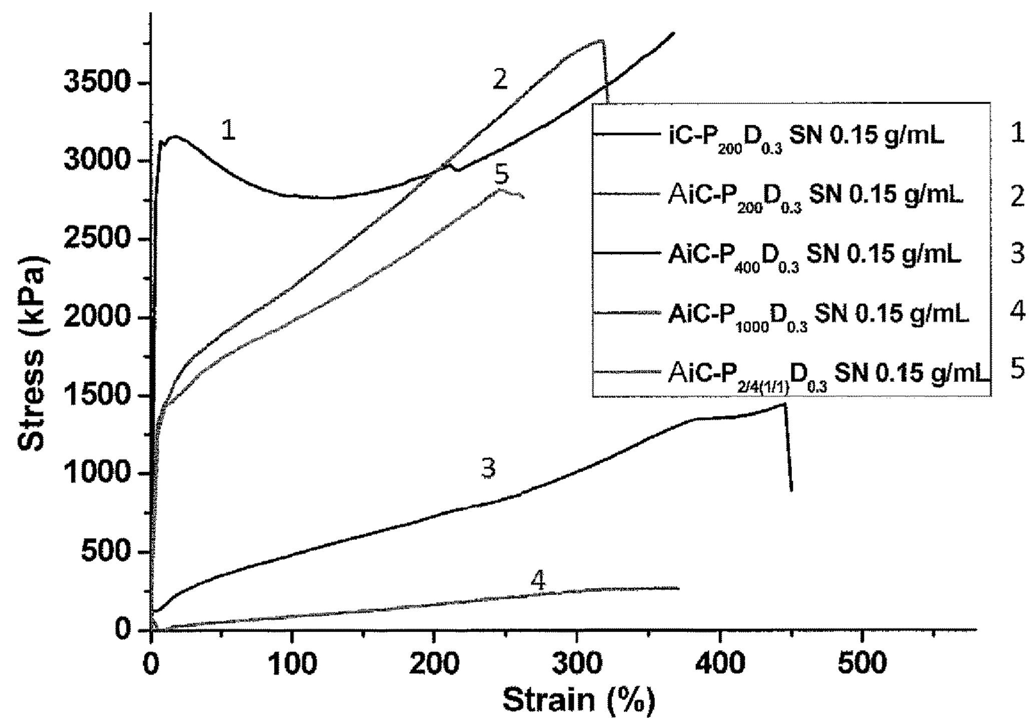
FIGS. 4A, 4B, 4C, and 4D each illustrate plots of physical and degradation properties of alkoxylated or alkenoxylated citrate-containing polymers according to some embodiments described herein.
Figure 4B:
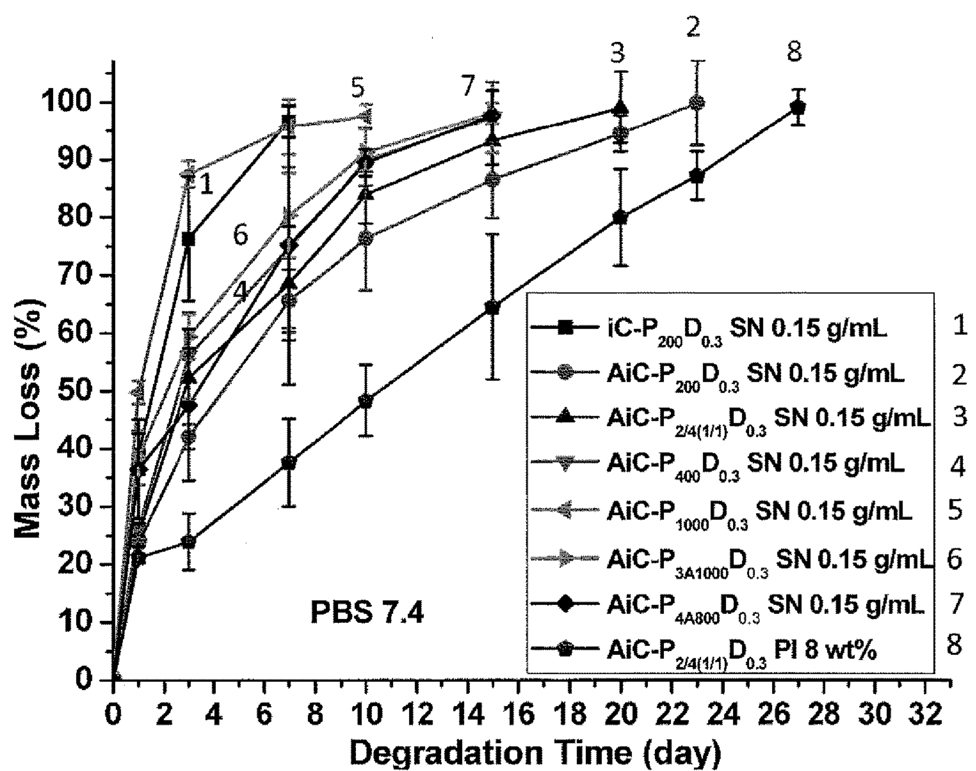
Figure 4C:
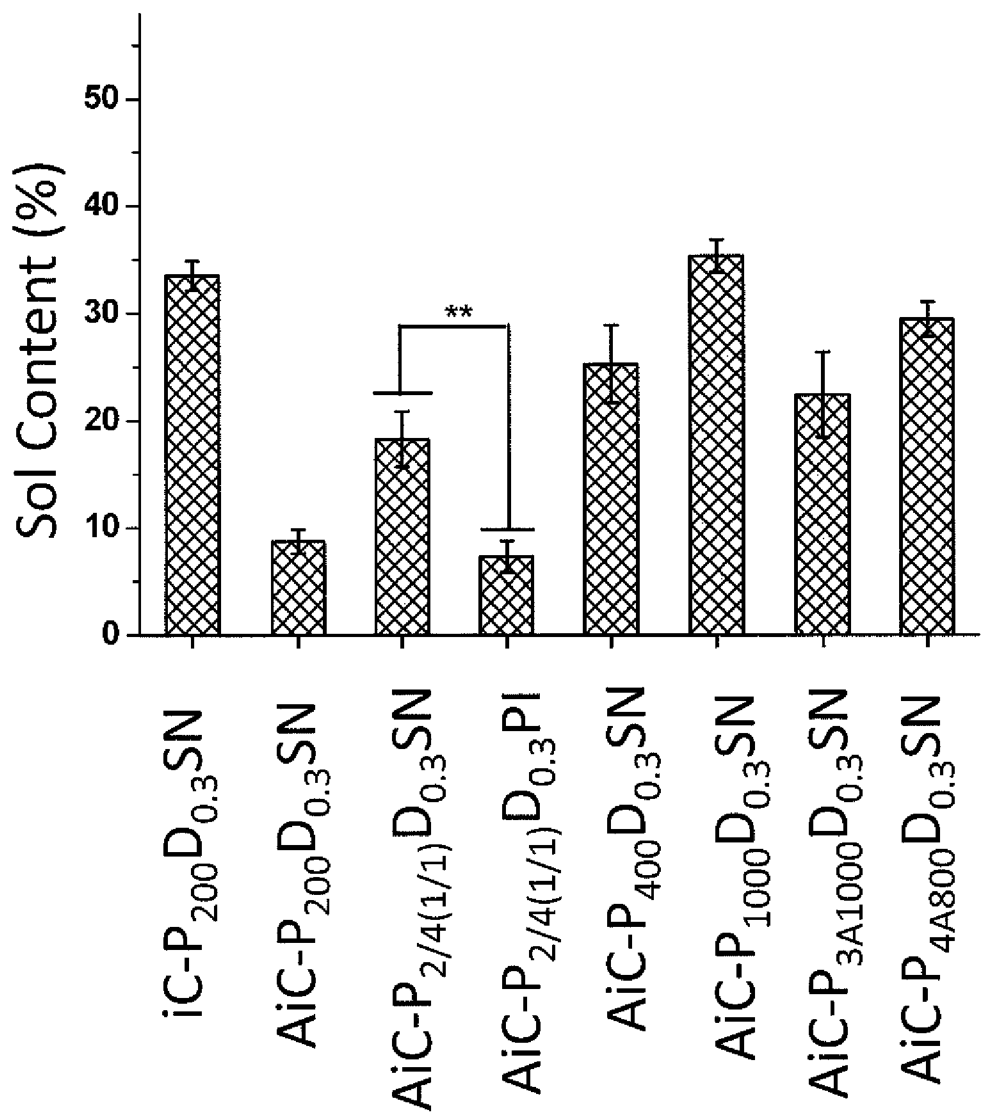
Figure 4D:
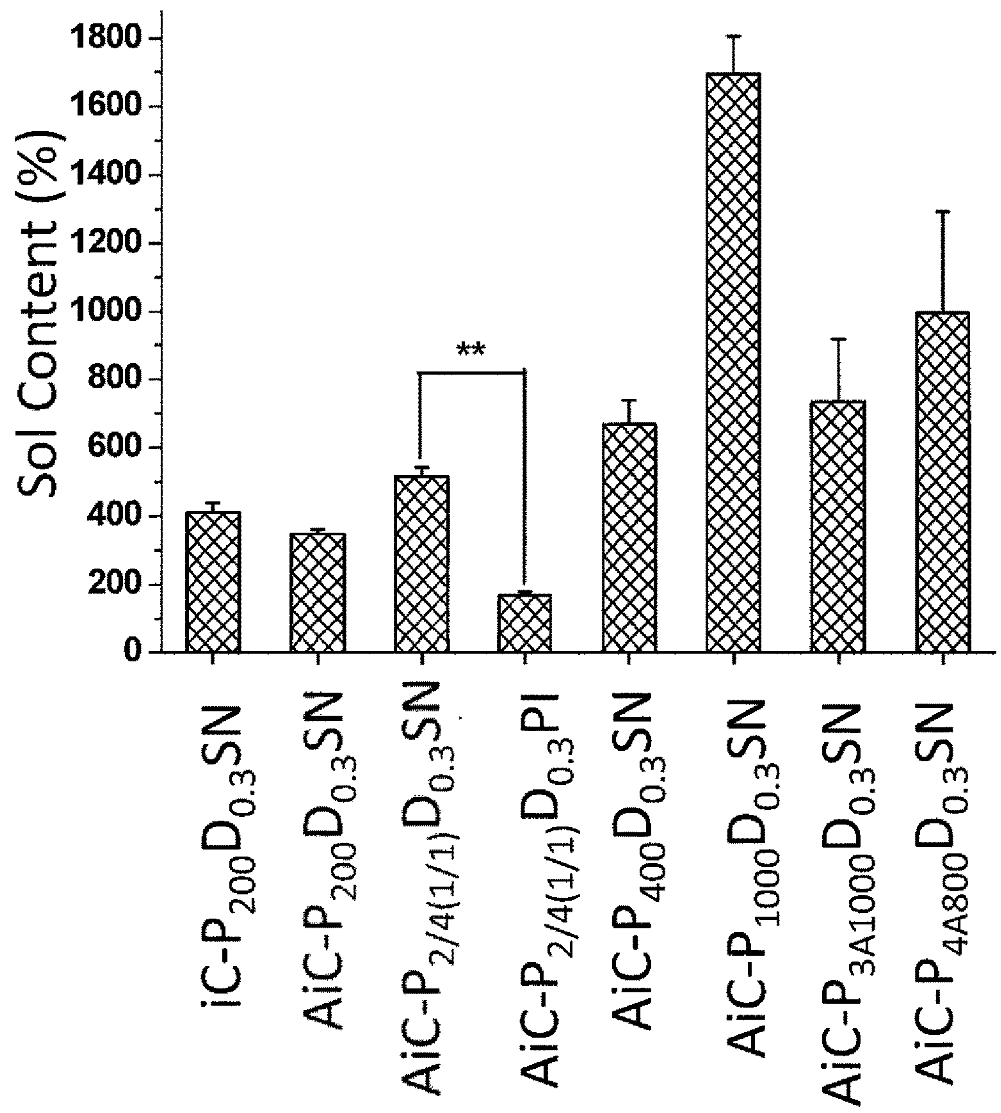

The cross-linking of AiC by SN was conducted as similar to a previously described method of Fullenkamp et al., *Biomaterials* 2012; 31:9092-105. The effect of pH value of iCMBA pre-polymer solution on the setting time was investigated using a representative polymer, iC-$P_{200}D_{0.3}$ (iCMBA formed by PEG200 without using U-CA, with a dopamine feeding ratio of 0.3 to PEG). The optimal pH value obtained by this study was 8.5. Thus, the cross-linking of AiC by SN was conducted at pH 8.5. Briefly, AiCs were dissolved in Tris-$HNO_3$ buffer solution (pH 13) with a concentration of 50 wt %, and the pH value was adjusted to 8.5. Then SN solution in Tris-FINO$_3$ buffer (pH 8.5) (for 1 g of pre-polymer, use 1 mL of SN solution) was added into AiC solution. Oxidation and consequently the cross-linking reaction of catechol-containing AiC were triggered upon mixing. Gelation or setting time of AiC was measured by a viscometry technique and the cross-linking of AiCs by PI was conducted as reported as described by Mehdizadeh et al., *Biomaterials* 2012; 33: 7972-83. Gelling times are shown in FIG. 3, and in Table 3 below.

TABLE 3

Gelling time of different AiCs and iCs cross-linked by various ratios of oxidants (silver nitrate, SN or sodium (meta) periodate, PI) under different pH values at room temperature (pre-polymer concentration was 50 wt % for all samples).

| Pre-polymer name [a] | Oxidant concentration used (g/mL) | Oxidant to pre-polymer ratio (g/g polymer) [b] | Test pH value [c] | Measured gel time (s) |
|---|---|---|---|---|
| iC-$P_{200}D_{0.3}$ | SN 0.15 | 0.15 | 2.8 | uncross-linkable |
| iC-$P_{200}D_{0.3}$ | SN 0.15 | 0.15 | 5 | 578 |
| iC-$P_{200}D_{0.3}$ | SN 0.15 | 0.15 | 7 | 363 |
| iC-$P_{200}D_{0.3}$ | SN 0.15 | 0.15 | 8.5 | 149 |
| AiC-$P_{200}D_{0.3}$ | SN 0.10 | 0.1 | 8.5 | 99 |
| AiC-$P_{200}D_{0.3}$ | SN 0.15 | 0.15 | 8.5 | 53 |
| AiC-$P_{400}D_{0.3}$ | SN 0.15 | 0.15 | 8.5 | 85 |
| AiC-$P_{1000}D_{0.3}$ | SN 0.15 | 0.15 | 8.5 | 193 |
| AiC-$P_{3A1000}D_{0.3}$ | SN 0.15 | 0.15 | 8.5 | 48 |
| AiC-$P_{4A800}D_{0.3}$ | SN 0.15 | 0.15 | 8.5 | 26 |
| AiC-$P_{2/4\ (1/1)}\ D_{0.3}$ | SN 0.15 | 0.15 | 8.5 | 66 [e] |
| AiC-$P_{2/4\ (1/1)}\ D_{0.3}$ | PI 8 wt % | 8 wt % to polymer | As it [d] | 126 [e] |

[a] For the ones cross-linked by silver nitrate (SN), pre-polymers were dissolved in 0.1M Tris-$HNO_3$ (pH 13) buffer with a concentration of 50 wt %; for those cross-linked by sodium periodate (PI), pre-polymer was dissolved in DI water with a 50 wt % concentration.

[b] Silver nitrate (SN) used was dissolved in 0.1M Tris-$HNO_3$ (pH 8.5) buffer, while sodium periodate (PI) was dissolved in DI water.

[c] For the ones cross-linked by SN, the tested pH values were adjusted using 12M NaOH and 70% nitric acid.

[d] Pre-polymer was dissolved in DI water (50 wt %) and used as is.

[e] Obtained by vial tilting method.

EXAMPLE 4

Properties of Cross-Linked Anti-Bacterial and Anti-Fungal iCMBAs

Physical and degradation properties of anti-bacterial anti-fungal injectable citrate-based mussel-inspired bioadhesives (AbAf iCs) cross-linked by silver nitrate (SN) or sodium periodate (PI) are shown in FIGS. 4A-4D. Mechanical properties (stress-strain curves, A), degradation profiles (B), leachable parts (sol content) (C), and swelling ratios (D) are depicted.

Mechanical properties of dried cross-linked AbAf iCs, including tensile strength, Young's modulus and elongation at break, were measured according to ASTM D412A on an Instron 5966 machine fitted with a 10 N load cell (Instron, Norwood, Mass.). Briefly, dog bone shaped samples (25 mm×6 mm×1.5 mm, length×width×thickness) were pulled at a rate of 500 mm/min and elongated to failure. The Young's modulus was obtained by calculating the gradient from 0 to 10% of elongation of the stress-strain curve. Eight specimens per sample were tested and averaged. In order to evaluate the effect of hydration on the mechanical properties, the mechanical tests were also conducted on fully swollen samples after being hydrated and swollen in water for 4 hrs. Table 4 shows the results of these tests on dried and swollen embodiments from Table 3, in which AiCs and iCs were cross-linked with silver nitrate (SN) with a test pH value of 8.5.

TABLE 4

Mechanical properties of dried and swollen embodiments from Table 3, where AiCs or iCs were cross-linked with silver nitrate (SN) and with a test pH value of 8.5.

| Pre-polymer name | Tensile strength (kPa) | | Elongation at break (%) | | Modulus (kPa) | |
|---|---|---|---|---|---|---|
| from Table 3 | Dry | Swollen | Dry | Swollen | Dry | Swollen |
| iC-$P_{200}D_{0.3}$ | 3432.6 ± 790.49 | 80.2 ± 6.74 | 375.6 ± 69.59 | 89.2 ± 17.4 | 106.9 ± 44.83 | 40.8 ± 5.93 |
| AiC-$P_{200}D_{0.3}$ | 3312.3 ± 495 | 120.2 ± 9.85 | 280.9 ± 35.30 | 119.2 ± 14.3 | 51561 ± 7712 | 82.4 ± 11.82 |
| AiC-$P_{2/4\ (1/1)}D_{0.3}$ | 2310.2 ± 105 | 92.2 ± 8.62 | 320.9 ± 25.30 | 108.1 ± 18.9 | 25681 ± 212 | 64.1 ± 10.93 |
| AiC-$P_{400}D_{0.3}$ | 1039.6 ± 300.0 | 41.2 ± 11.03 | 415.6 ± 87.52 | 89.8 ± 28.1 | 592.0 ± 104.0 | 31.2 ± 16.71 |
| AiC-$P_{1000}D_{0.3}$ | 163.4 ± 70.61 | 71.2 ± 12.31 | 400.5 ± 35.27 | 119.3 ± 19.2 | 189.6 ± 81.34 | 26.2 ± 7.22 |
| AiC-$P_{4A800}D_{0.3}$ | 459.7 ± 95.06 | 67.2 ± 13.10 | 321.3 ± 74.23 | 104.1 ± 9.3 | 1435.9 ± 7.56 | 23.1 ± 6.15 |

The sol/gel content, an indication of non-crosslinked/crosslinked fractions of the hydrogel, and swelling ratio were measured by the mass differential before and after incubation of the cross-linked polymer in 1, 4-dioxane (sol content) or water (swelling ratio) as described above. The sol content and swelling ratio were then calculated using equations (2) and (3), respectively.

$$\text{Sol content (\%)} = \frac{W_i - W_d}{W_i} \times 100 \quad \text{Equation (2)}$$

$$\text{Swelling ratio (\%)} = \frac{W_s - W_d}{W_d} \times 100 \quad \text{Equation (3)}$$

Here $W_i$ represents the initial dry weight of cross-linked hydrogel disk, $W_d$ represents the weight of freeze-dried sample after the uncross-linked part was washed by 1, 4-dioxane for 48 hrs, and $W_s$ represents the network weight after the leached and dried sample was suspended in water for 24 hrs.

Degradation studies were conducted in PBS (pH 7.4) and at 37° C. using cylindrical disc specimens (7 mm in diameter, 2 mm thick). The mass loss was calculated by comparing the initial mass ($W_0$) with the mass measured at the pre-determined time points ($W_t$) using equation (1) above.

Figure 5:
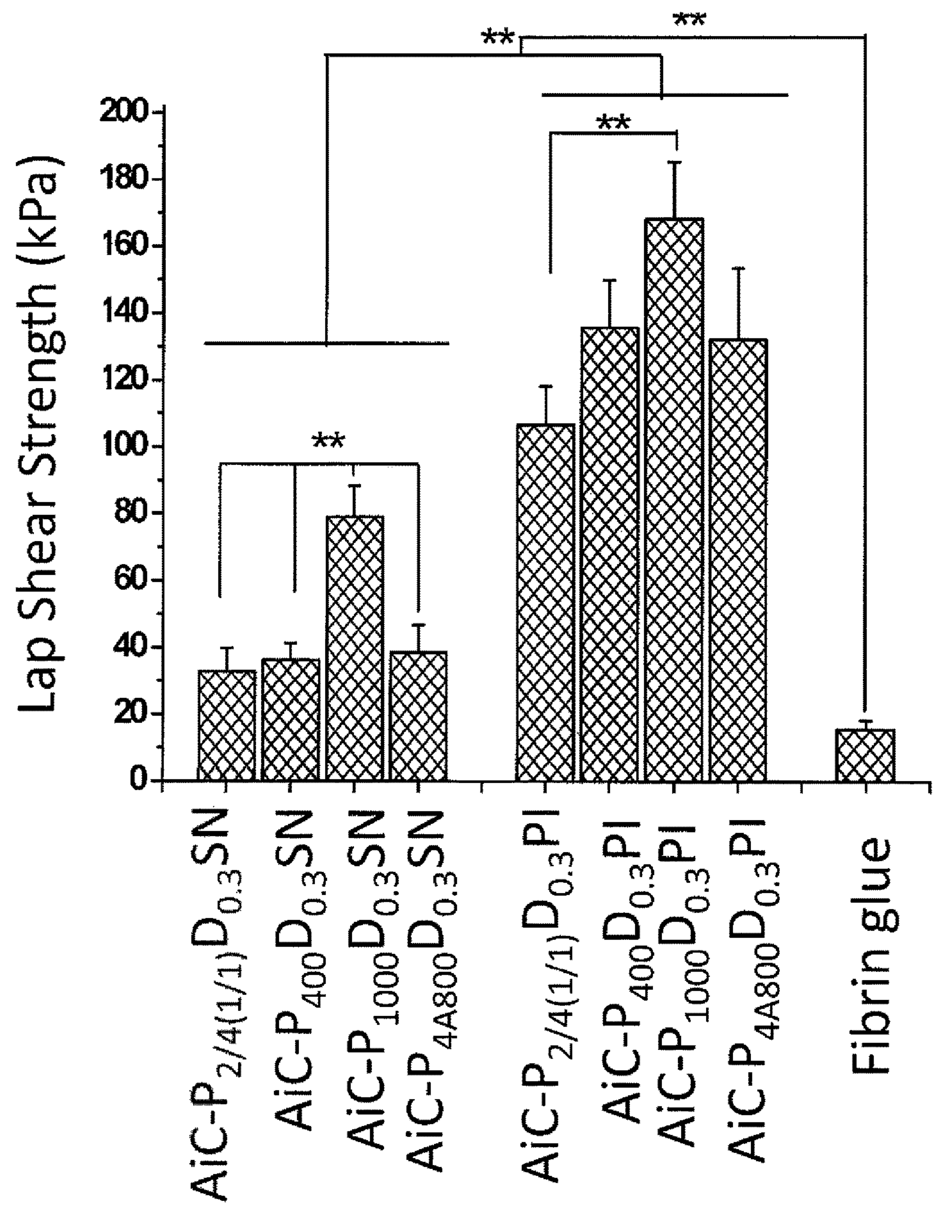
FIG. 5 illustrates graphs of adhesion properties of alkoxylated or alkenoxylated citrate-containing polymers according to some embodiments described herein.

The adhesion strength of AbAf iCs cross-linked by SN or PI was determined by the lap shear strength test according to the modified ASTM D1002-05 method as described in Mehdizadeh et al., *Biomaterials* 2012; 33: 7972-83. The results are shown in FIG. 5, where adhesion strength of AbAf iCs cross-linked by silver nitrate (SN) or sodium periodate (PI), and the adhesion strength of fibrin glue, to wet porcine small intestine submucosa were measured by lap shear strength tests (p<0.01). The results from FIG. 5** are also included in Table 5 below.

TABLE 5

Wet tissue adhesion strength of different AbAfiCs cross-linked with silver nitrate (SN) or sodium periodate (PI), and of fibrin glue, on porcine small intestine submucosa measured by lap shear strength test.

| Pre-polymer name [a] | Oxidant used and amount | Lap shear strength (kPa) |
|---|---|---|
| AiC-$P_{2/4(1/1)}D_{0.3}$ | SN 0.15 g/g polymer [b] | 32.85 ± 7.03 |
| AiC-$P_{2/4(1/1)}D_{0.3}$ | PI 8 wt % [c] | 106.43 ± 11.58 |
| AiC-$P_{400}D_{0.3}$ | SN 0.15 g/g polymer [b] | 36.21 ± 5.14 |
| AiC-$P_{400}D_{0.3}$ | PI 8 wt % [c] | 135.49 ± 14.28 |
| AiC-$P_{1000}D_{0.3}$ | SN 0.15 g/g polymer [b] | 79.04 ± 9.28 |
| AiC-$P_{1000}D_{0.3}$ | PI 8 wt % [c] | 168.15 ± 17.02 |
| AiC-$P_{4,4800}D_{0.3}$ | SN 0.15 g/g polymer [b] | 38.50 ± 8.23 |
| AiC-$P_{4,4800}D_{0.3}$ | PI 8 wt % [c] | 132.15 ± 21.12 |
| Fibrin glue | — | 15.38 ± 2.82 |

[a] Pre-polymer concentrations were all 50 wt %. For bioadhesives cross-linked by SN, pre-polymers were dissolved in Tris-$HNO_3$ buffer and the pH values were adjusted to 8.5 before use.
[b] SN concentration was 0.15 g/mL in pH 8.5 Tris-$HNO_3$ buffer.
[c] PI concentration was 8 wt % in DI water, and PI to pre-polymer ratio was also 8 wt %.

EXAMPLE 5

Cytocompatibility Tests of AiC Pre Polymers and Cross-Linked AbAf iC Hydrogels

Human-derived mesenchymal stem cells (hMSCs, ATCC® PCS-500-012TM) were purchased from ATCC, and passages 5-10 were used for cytotoxicity study in this work. In vitro pre-polymer cytotoxicity was assessed by MTT (methylthiazolyl-diphenyl-tetrazolium bromide) assay against hMSCs. First, different AiC pre-polymers were dissolved into complete Dulbecco's modified eagle's medium (DMEM, with 10% (v/v) fetal bovine serum (FBS) and 1% (v/v) antibiotic antimycotic solution (100×)), namely growth media (MG), with a pre-polymer concentration of 10 mg/mL, and the pH value of the solutions was adjusted to 7.4 before use. Then the 10 mg/mL pre-polymer solutions in MG were diluted 10 and 100 times by blank MG media to make a pre-polymer containing MG solution with a final concentration of 1 and 0.1 mg/mL respectively. Next, to each well of a 96-well cell culture plate, 200 μL of hMSC solution in MG, with a density of $5\times10^4$ cells/mL, was added and incubated for 24 hrs at 37° C., 5% $CO_2$ and 95% relative humidity. Twenty four hours post cell seeding, the medium was completely replaced by 200 μL of pre-polymer containing MG media with various concentrations (10, 1, and 0.1 mg/mL), and incubated for another 24 hrs followed by MTT assay. Poly (ethylene glycol) diacrylate (PEGDA, $M_n$=700 Da) solutions with the same weight concentrations were used as negative controls. Viabilities of cells in pre-polymer or PEGDA containing MG media were normalized to that of cells cultured in blank MG media. Cytotoxicity of CA and PI with different concentrations was also assessed using the same method.

The cytotoxicity of sol contents (or leachable fractions) and degradation products of AbAf iC hydrogels, cross-linked by SN or PI, were also studied using MTT assay against hMSCs, with iCMBA-$P_{200}D_{0.3}$ PI 8 wt % as a control. The sol content solution of AbAf iC hydrogel was obtained by incubating equal mass (0.5 g) hydrogel specimens in 5 mLs of PBS (pH 7.4) at 37° C. for 24 hours. Next, three different solutions were prepared: 1×, 10× and 100× (1× was the solution of leached products with no dilution; 10× and 100× means 10 times and 100 times dilution of 1× solution by PBS, respectively). To each well of a 96-well cell culture plate, 200 μL of hMSC solution in MG medium with a density of $5\times10^4$ cells/mL was added and incubated for 24 hours. Then, 20 μL of sol content solutions with various concentrations were added and the cells were incubated for another 24 hrs followed by MTT assay.

The cytotoxicity of degradation products of AbAf iC hydrogels was also evaluated. Equal weight (1 g) of AbAf iC hydrogel samples as well as poly (lactic-co-glycolic acid) (PLGA, used as control, LA/GA=50/50, Mw~60 KDa, purchased from Polyscitech) were fully degraded in 10 mL of 0.2 M NaOH solution. After adjusting pH value to 7.4, the resultant solutions were diluted to three concentrations (1×, 10× and 100×) using PBS (pH 7.4), and used for cell culture (the process was the same as used in sol content cell cytotoxicity study described above) and subsequent MTT analysis.

All the above solutions were pH-neutralized and passed through a sterilized 0.2 μm filter prior to use for cell culture. The cell viability results were normalized to the viability of cells in blank MG medium.

Figure 6A:
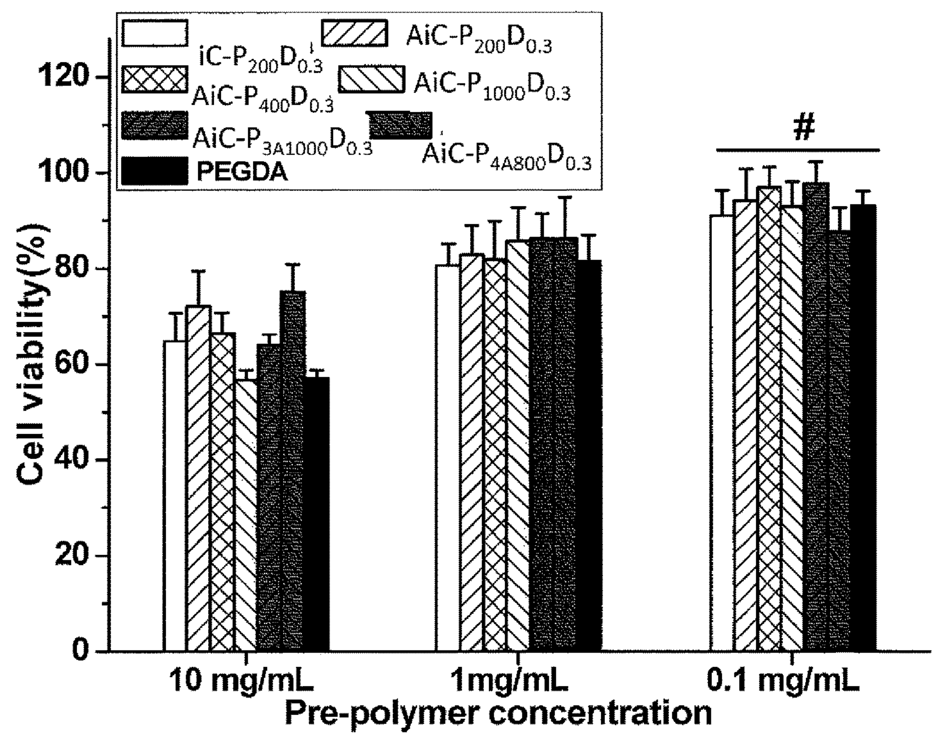
FIGS. 6A, 6B, 6C, and 6D each illustrate graphs of cytotoxicity of alkoxylated or alkenoxylated citrate-containing polymers according to some embodiments described herein.
Figure 6B:
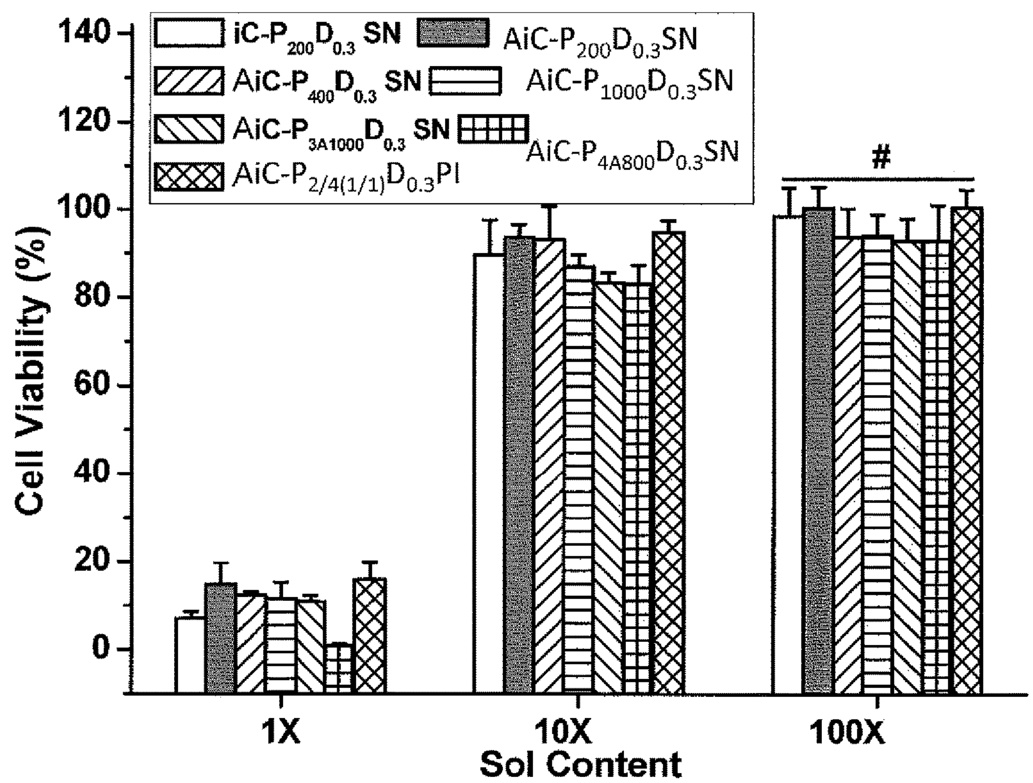
Figure 6C:
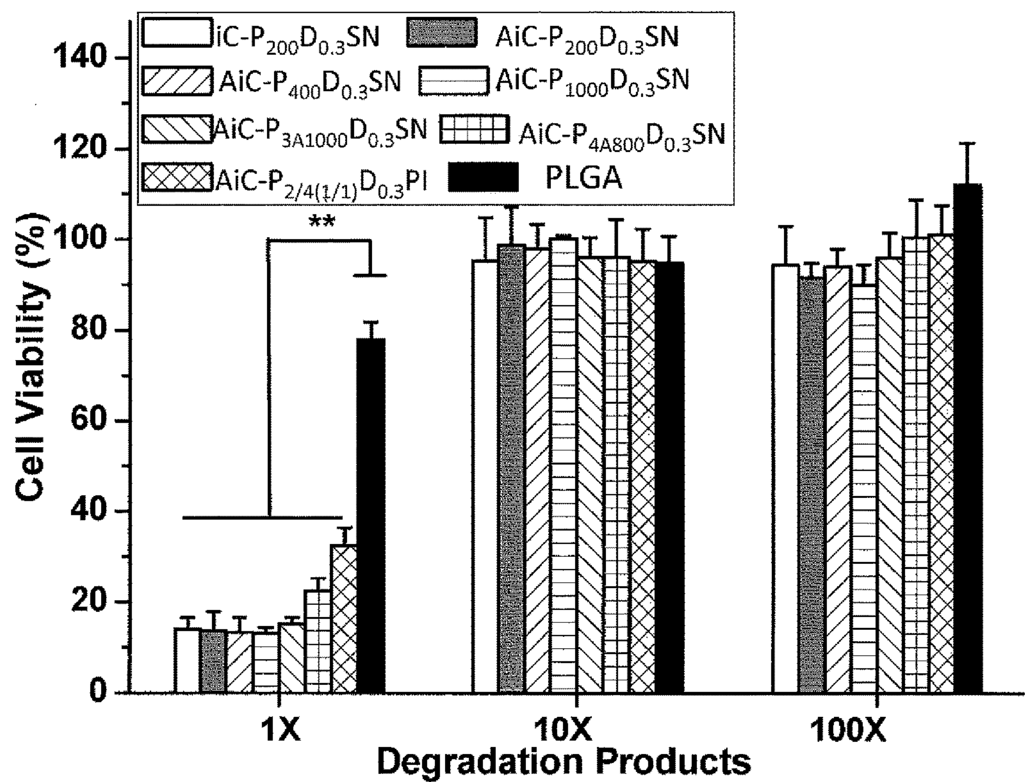
Figure 6D:
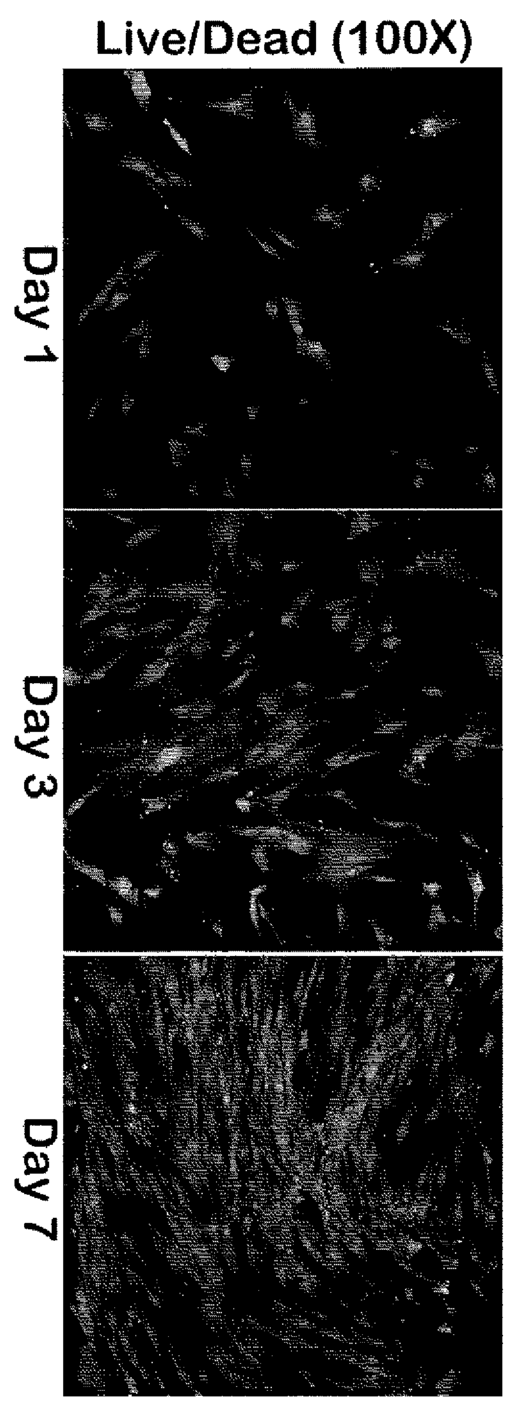
Figure 7A:
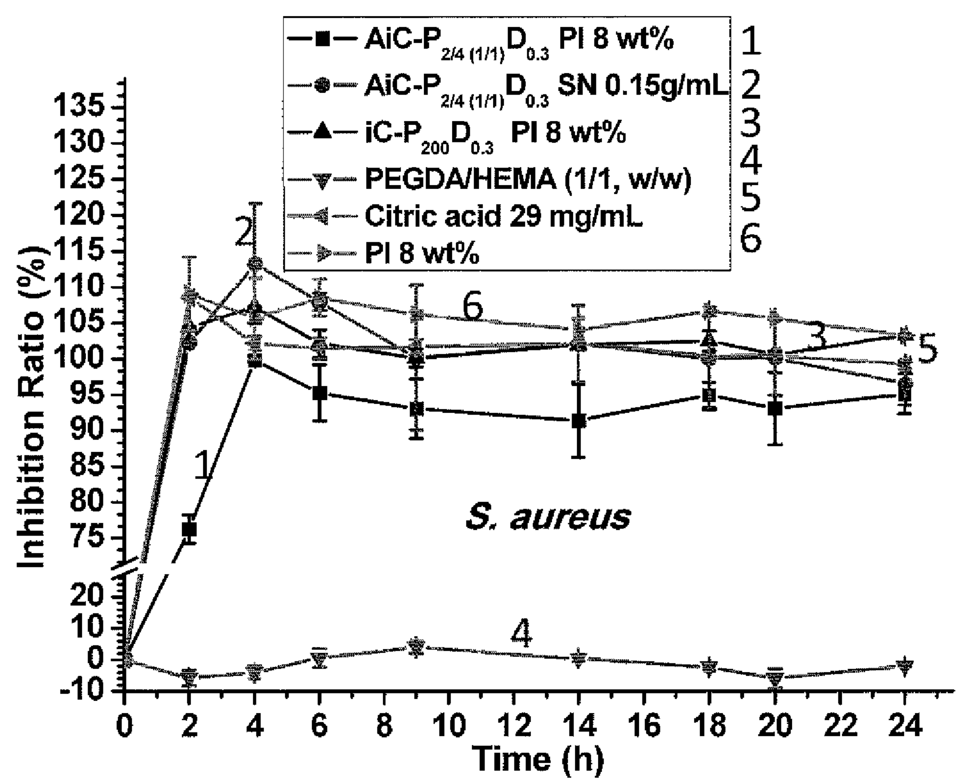
FIGS. 7A, 7B, 7C, and 7D each illustrate antibacterial properties of alkoxylated or alkenoxylated citrate-containing polymers according to some embodiments described herein.
Figure 7B:
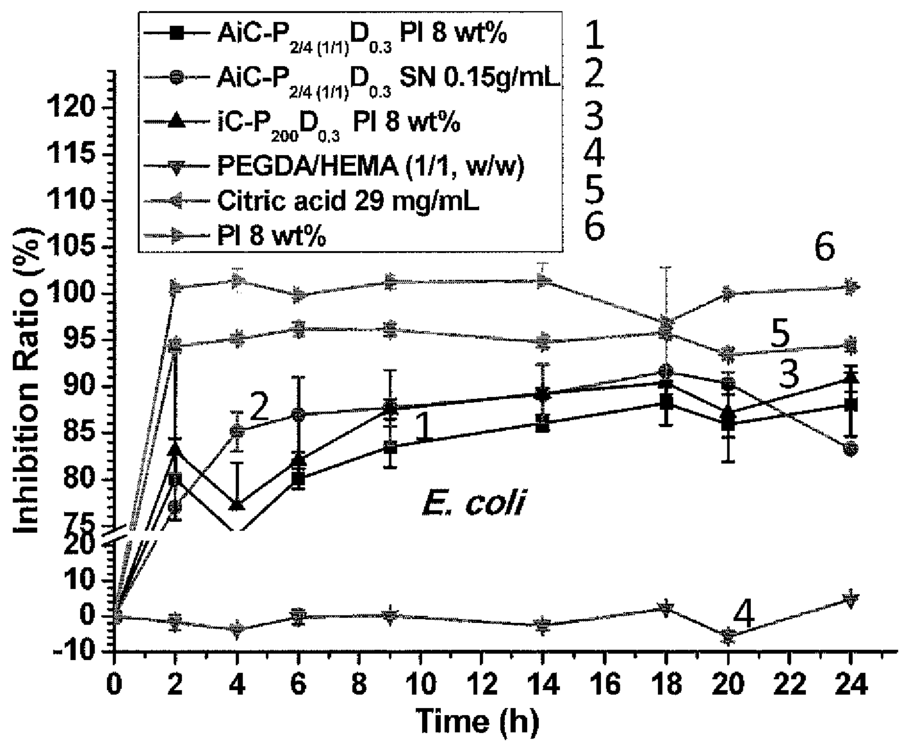
Figure 7C:
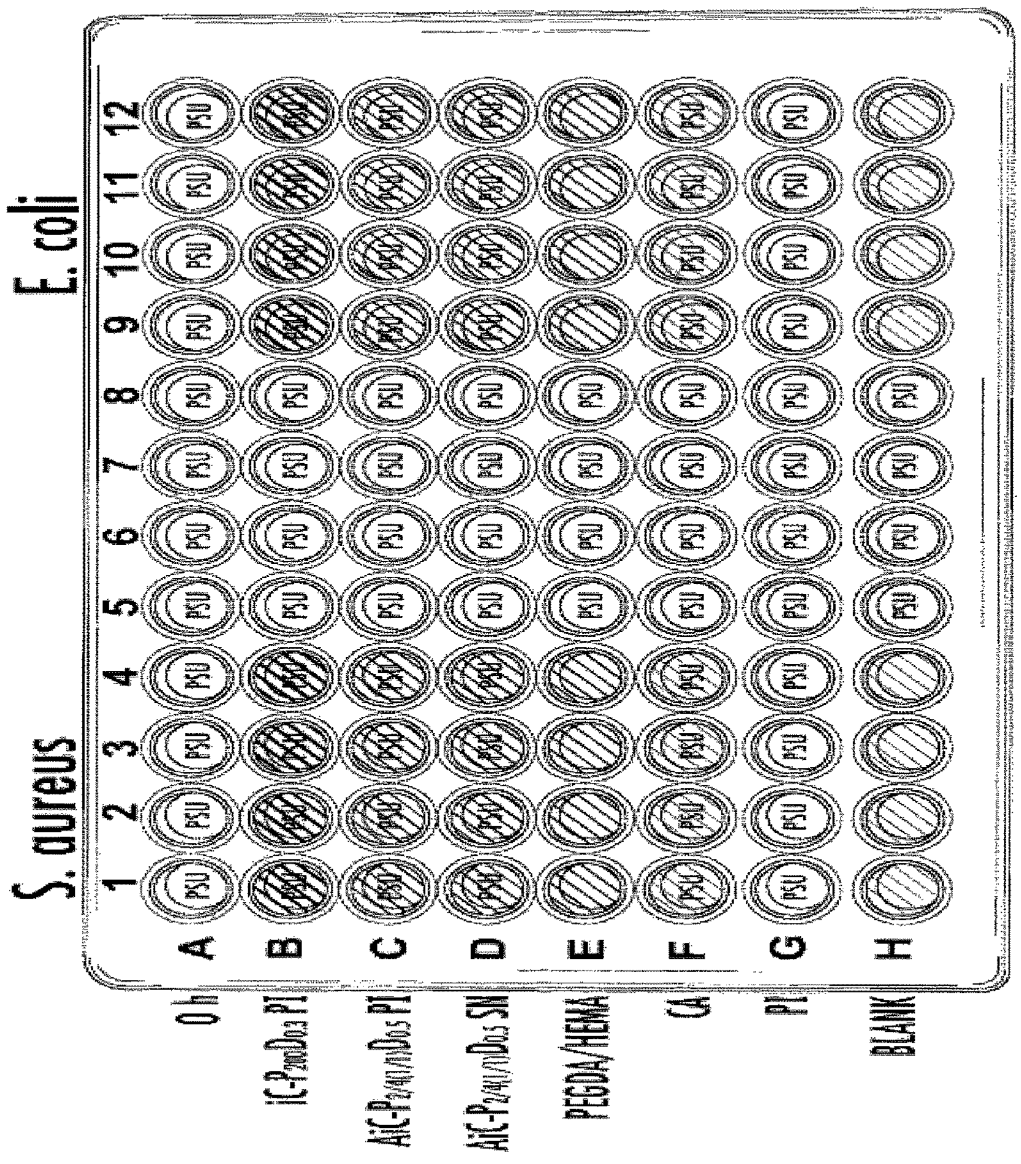
Figure 7D:
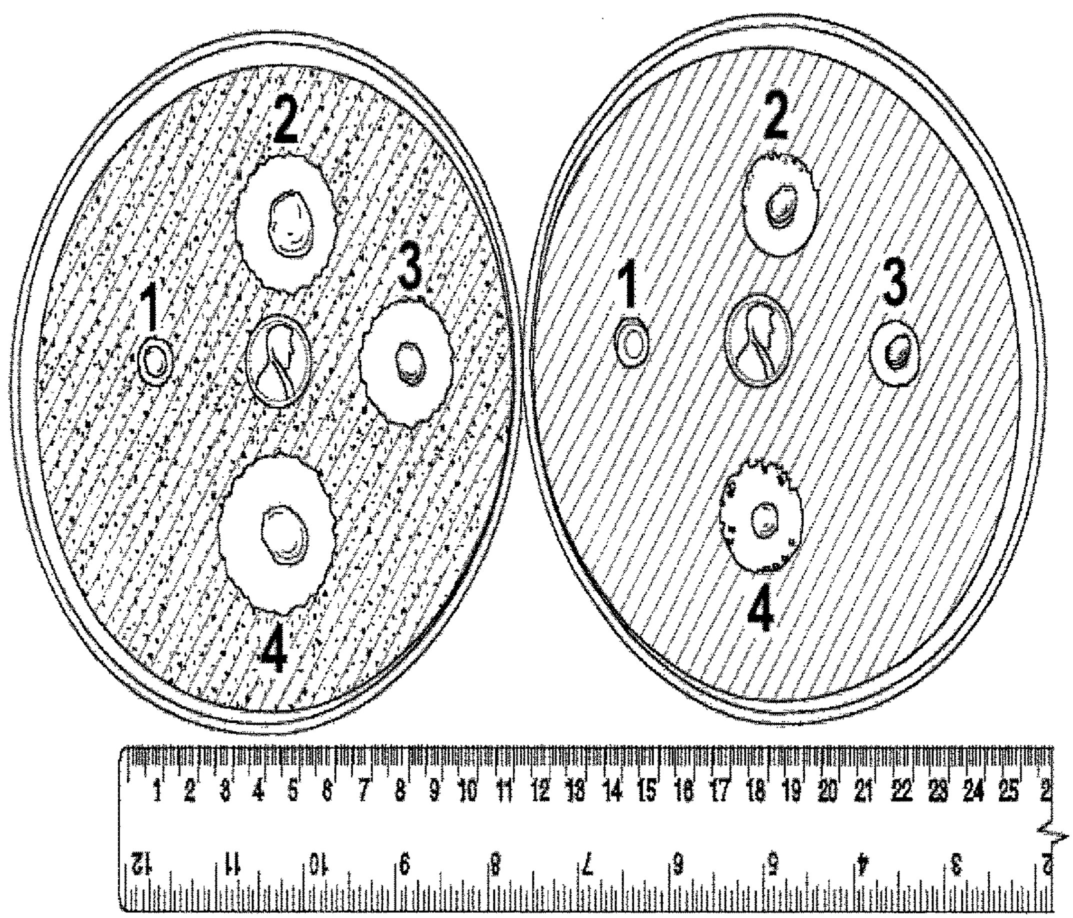

Cell adhesion and proliferation on cross-linked AbAf iC films was also studied against hMSC cells. The morphology of hMSC cells was observed by Live/Dead staining assay. Briefly, about 20 μL of AbAf iC mixture (containing AiC pre-polymer and oxidant, SN or PI) (prior to completion of cross-linking) was uniformly spread on the surface of a glass slide with a diameter of 15 mm to form a thin layer of the cross-linked AbAf iC. The samples were then sterilized by incubation in 70% ethanol for 24 hrs followed by exposure to UV light for 3 hrs. The samples were then placed in 24-well plates and seeded with 500 μL hMSC solutions with a density of 5,000 cells/$cm^2$ followed by MG media replacement the next day. At each time point (1, 3 and 7 days post cell seeding), the constructs were removed from the well plate, rinsed by PBS, and stained by Live/Dead Viability/Cytotoxicity Kit (Invitrogen, molecular probes, Eugene, Oreg.) for the observation of cell morphology using an inverted light microscope (Nikon Eclipse Ti-U) equipped with a ANDOR DL-604M-#VP camera and Prior Lumen 200. The results are shown in FIG. 6, as follows: (A) anti-fungal iCMBA pre-polymers, (B) leachable part (sol content), and (C) degradation product. FIG. 6D shows cell morphology on AbAf iCMBA films by Live/Dead staining at $1^{st}$, $3^{rd}$, and $7^{th}$ day post-seeding.

EXAMPLE 6

Anti-Bacterial Performance of AbAf iC Bioadhesives

Bacterial incubation: *Staphylococcus aureus* (*S. aureus*, ATCC® 6538™) and *Escherichia coli* (*E. coli*, ATCC® 25922™) were purchased from ATCC (American Type Culture Collection) and used following established safety protocols. Tryptic soy broth (Cat. #: C7141) and tryptic soy agar (Cat. #: C7121) used for *S. aureus* culture were purchased from Criterion (through VWR). Luria broth base (LB broth, Cat. #: 12795-027) and select agar (Cat. #: 30391-023) used for *E. coli* culture were purchased from Invitrogen. *S. aureus* and *E. coli* were cultivated at 37° C. in sterilized tryptic soy broth and LB broth respectively with a speed of 150 rpm in a rotary shaker overnight and the obtained bacteria suspensions were diluted into various concentrations before use.

Bacterial Inhibition Kinetics Curves:

To examine the kinetics of bacterial growth and the inhibition ratio of AbAf iC hydrogels cross-linked by SN or PI, AiC-$P_{2/4(1/1)}D_{0.3}$ SN 0.15 g/mL (AiC-SN) and AiC-$P_{2/4(1/1)}D_{0.3}$ PI 8 wt % (AiC-PI) were chosen as the representative experimental groups, and iCMBA-$P_{200}D_{0.3}$ PI 8 wt % (iC-PI) and PEGDA/HEMA hydrogels ($M_n$ of PEGDA is 700 Da, w/w between PEGDA and 2-Hydroxyethyl methacrylate (HEMA)=1/1, cross-linked by APS and TEMED) were used as controls. Citric acid (29 mg/mL) and PI (8 wt %) solutions were also tested. The bacterial inhibition kinetics to both *S. aureus* and *E. coli* were tested. For each hydrogel sample, 0.2 g of freeze-dried hydrogel was immersed in 20 mL of germ containing nutrient solution with a bacterial concentration of optical density (OD) at 600 nm around 0.1. Incubation was performed at 37° C. with an orbital shaker with a speed of 150 rpm for 24 hrs. Pure growth broth without bacterials was also tested and served as a control. The bacterial broth medium was taken out at pre-set intervals (200 μL each time), and the OD value of the medium at 600 nm was recorded by a microreader (TECAN, infinite M200 PRO). The inhibition ratios of hydrogels or other supplements (CA or PI) were calculated by equation (4):

$$\text{Inhibition ratio } (\%) = 100 - 100 \times \frac{A_t - A_0}{A_{con} - A_0} \qquad \text{Equation (4)}$$

Where 4 was the OD value of bacterial broth medium before incubation, and $A_t$ and $A_{con}$ were the OD values of hydrogel/supplement-containing medium and pure medium (control) after incubation for the designated time, respectively.

Zone of Inhibition Against Bacteria Test:

AiC-SN, AiC-PI, and iC-PI, as well as PEGDA/HEMA hydrogel, were used to test anti-bacterial inhibition halos by modified Kirby Bauer technique (see Zhou et al., *Radiat. Phys. Chem.* 2012; 81: 553-60; and Yu et al., *J Appl Polym Sci* 2007; 103: 125-33.). Briefly, 10 mL of bacteria medium (with an OD value at 600 nm around 0.1, both *S. aureus* and *E. coli* were tested) was dispensed onto a tryptic soy/LB agar plate (Φ140×7 mm). Then Hydrogel disks (around (Φ5×3 mm) were placed on the agar plate and incubated for 24 hrs at 37° C. After incubation, the bacterial inhibition halos around the hydrogel samples were observed and their diameters were measured.

Minimal Inhibitory Concentration (MIC) Tests of CA, UA, and PI Against Bacteria:

The minimal inhibitory concentrations (MICs) of citric acid (CA), buffered CA (pH 7.4), 10-undecylenic acid (UA), and PI against *S. aureus* and *E. coli* were measured using the broth macrodilution method (using 2× gradient dilution). Bacteria were incubated at 37° C. for 24 hrs. Bacterial survival ratios were calculated by equation (4), and the MICs were determined as the lowest drug concentrations that induced complete inhibition of bacteria growth.

Anti-Bacterial Properties of Degradation Products and Release Solutions of AbAf iC Bioadhesives:

To evaluate the long-term effect of AbAf iC hydrogels on bacteria, the anti-bacterial properties of degradation products and periodical release solutions of AbAf iC hydrogels were tested, using iC-PI and PEGDA/HEMA as controls.

For the anti-bacterial evaluation of degradation products, 1 g of freeze-dried hydrogel was fully degraded in 10 mL 0.2 M NaOH solution, and then diluted into 1×, 10× and 100× solutions after adjusting the pH to 7.4 and sterilization by filtering through a 0.2 μm filter (1× means no dilution, 10× and 100× means being diluted 10 and 100 times respectively by tryptic soy broth/LB broth). For the bacteria inhibition ratio test, degradation product solutions (with various dilutions) were added in the wells of 24-well plates with 450 per well. 50 μL of bacteria suspension was added into each well to give initial bacteria concentration of $OD_{600nm}$ around 0.1. Control samples were established by diluting 50 μL of the same bacteria suspension in 450 μL of blank broth medium. The 24-well plates were incubated at 37° C. for 24 hrs with a shaking speed of 150 rpm followed by OD value recording. The bacteria inhibition ratio was calculated by equation (4).

For release solution anti-bacterial evaluation, 0.1 g freeze-dried hydrogel was placed into a sterilized 15-mL centrifuge tube after being sterilized by UV for 30 min, and 5 mL of tryptic soy broth or LB broth was added to the tube. The hydrogel suspension was shaken at 37° C., and the periodical release solutions were collected after shaking for 4, 8, and 14 days (broth medium was totally replaced at each time point). The bacteria inhibition ratios of these periodical release solutions were measured using the same method described in the bacterial inhibition ratio test of degradation products.

Results are shown in FIG. 7. Anti-bacterial performance of AbAf iCMBAs is demonstrated in inhibition ratios kinetics curves of cross-linked AbAf iCMBAs, iC-$P_{200}D_{0.3}$ PI 8 wt %, PEGDA/HEMA (w/w=1/1, as control), and citric acid (CA, 29 g/mL) as well as sodium periodate (PI, 8 wt %) against *S. aureus* (FIG. 7A) and *E. coli*. (FIG. 7B). FIG. 7C shows an image of bacteria in broth media before and after being directly exposed to cross-linked AbAf iCMBAs, CA (29 mg/mL) and PI (8 wt %) for 24 hrs; note that the 96-well plate was placed on a piece of paper with one "PSU" symbol underneath each well. FIG. 7D shows inhibition halos of cross-linked hydrogels after 24 hrs incubation at 37° C. (D), 1. PEGDA/HEMA (w/w 1/1), 2. iC-$P_{200}D_{0.3}$ PI 8 wt %, 3. AiC-$P_{2/4(1/1)}D_{0.3}$ PI 8 wt %, and 4. AiC-$P_{2/4(1/1)}D_{0.3}$ SN 0.15 g/mL.

EXAMPLE 7

Anti-Fungal Performance of AbAf iC Bioadhesives

Fungi Incubation:

Fungi (*Candida albicans, C. albicans*, ATCC® 10231™) was used following established safety protocols. YM medium broth (Lot #: 1964C030) and YM agar (Lot #: 1964C030) used for fungi (*C. albicans*) culture were obtained from Amresco and Acumedia separately through VWR. Tween 20 was added to YM broth medium with a final concentration of 0.5 wt % and sterilized before being used for fungi culture in broth (the addition of Tween 20 can stabilize the suspension of fungi in YM broth). In all cases, *C. albicans* was maintained on YM agar plates. For experiments, *C. albicans* was scraped from YM agar plates and dispersed in Tween 20 containing YM broth medium, counted with a hemocytometer, and diluted into a final fungi concentration of $0.5\text{-}1\times10^7$ cells/mL. The actual measure of fungal survival used a colony growth assay on YM agar plates is described in detail below.

Anti-Fungal Effect of Direct Exposure to Hydrogels:

The anti-fungal effect of direct exposure to AbAf iC hydrogels was tested using AiC-SN and AiC-PI as representative experimental groups, and iC-PI and PEGDA/HEMA hydrogels as controls. Briefly, 10 mg freeze-dried hydrogel disks were placed in the wells of a 24-well tissue culture plate, and 1 mL of *C. albicans* suspension in Tween-20 containing YM broth medium ($0.5\text{-}1\times10^7$ cells/mL) was added to each well. Samples without hydrogel were used as blank controls. The 24-well plates were incubated for 3 hrs at 37° C. with shaking speed of 100 rpm. Then the hydrogel disks were removed, the remaining medium was diluted 300 times, and 0.3 mL diluted medium was removed and cast on YM agar plates (Φ6×2 mm). After incubation at 37° C. for 24 hrs, fungi colonies on the YM agar plates were counted, and the fungi survival ratios were calculated according to equation (5). For each sample, at least 6 plates were cast, and the numbers were averaged.

$$\text{Fungal survival ratio (\%)} = \frac{N_s}{N_{con}} \times 100 \qquad \text{Equation (5)}$$

Here, $N_s$ stands for the number of fungal colonies for samples, and $N_{con}$ stands for the number of fungal colonies for YM broth blank control.

Halo Test:

The anti-fungal performance of AiC-SN and AiC-PI was also tested by the halo test method using iC-PI and PEGDA/HEMA hydrogels as controls. Briefly, 4 mLs of YM broth medium containing $0.5\text{-}1\times10^7$ cells/mL *C. albicans* was evenly cast onto YM agar plates (Φ85×6 mm). The hydrogel discs (around Φ5×3 mm) were placed on the agar plate and the constructs were incubated at 37° C. for 24 hrs in the dark before being examined for a "halo" or "zone of inhibition" surrounding the gel disc.

Minimal Inhibitory Concentrations (MICs) Tests of CA, UA, and PI Against Fungi:

The MICs of CA, buffered CA (pH 7.4), UA, PI, and AiC-$P_{2/4(1/1)}D_{0.3}$ as well as iCMBA-$P_{200}D_{0.3}$ pre-polymers to *C. albicans* were measured using the agar dilution method (using 2× gradient dilution) [19]. CA or other samples in YM agar with various concentrations were injected into the wells of 6-well tissue culture plates when the hot YM agar solution was still flowable (3 mLs each well). After solidification, fungi suspension in YM broth ($0.5\text{-}1\times10^5$) was spread onto YM agar (0.3 mLs each well), and the plates were incubated at 37° C. for 24 hrs. The fungi survival ratios were calculated by equation (5), and the MICs were determined as the lowest drug concentrations that induced complete inhibition of fungi growth.

Anti-Fungal Properties of Degradation Products and Release Solutions of AbAf iC Bioadhesives:

The anti-fungal properties of degradation products and periodical release solutions of AbAf iCs were tested using AiC-SN and AiC-PI as representative experimental groups. iC-PI and PEGDA/HEMA were used as controls. Degradation solutions with various dilutions and periodical release solutions were obtained using the same protocol as in the corresponding anti-bacterial study, using YM broth instead of tryptic soy/LB broth. Degradation products with different dilutions or periodical release solutions collected at different time points were put in the wells of 24-well tissue culture plates (450 μL per well), with blank YM broth samples as control. 50 μL of *C. albicans* suspension in Tween-20 containing YM broth medium was added to each well, with the initial fungi concentration kept in the range of $1.5\text{-}1\times10^7$ cells/mL. The 24-well plates were incubated at 37° C. for 3 hrs with shaking at 100 rpm. The resulting solution was diluted 300 times, and cast on YM agar plates. After incubation at 37° C. for 24 hrs, fungi colonies on the YM agar plates were counted, and the fungal survival ratios were calculated according to equation (5).

Figure 8A:
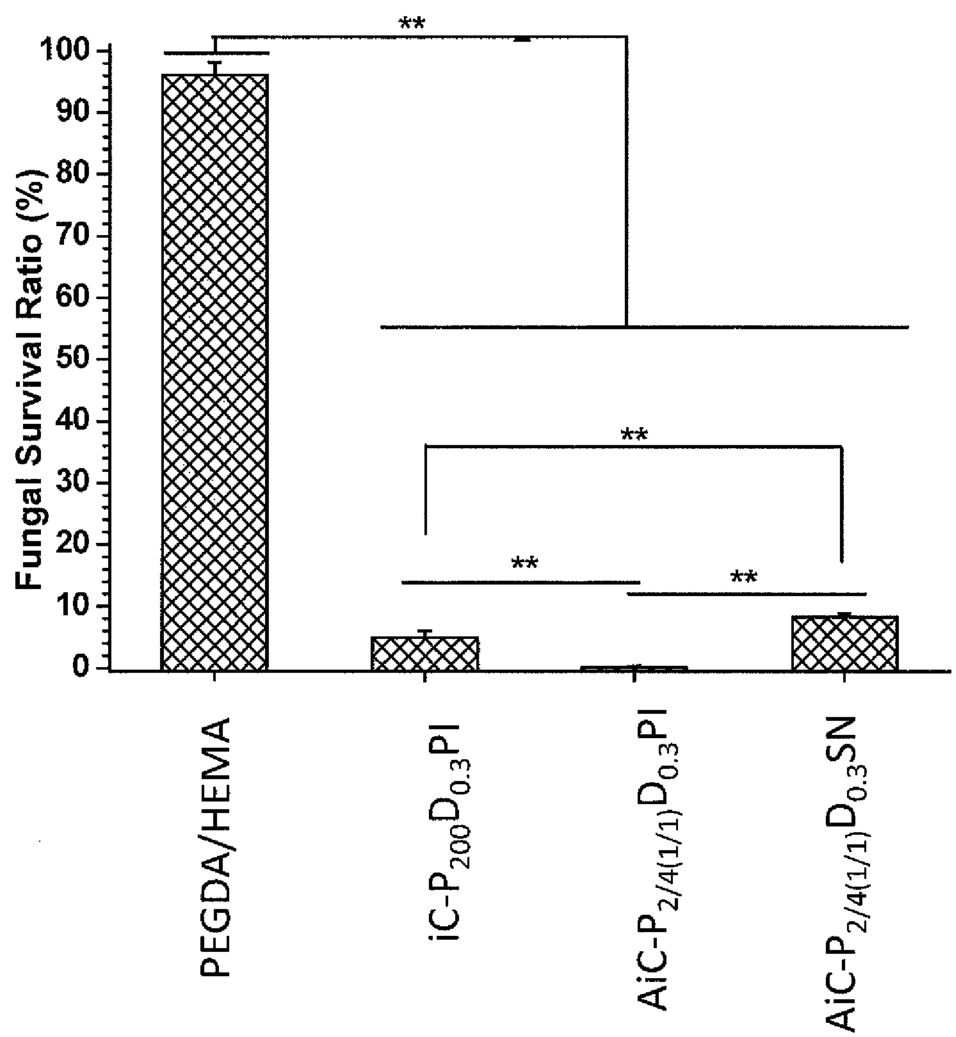
FIGS. 8A and 8B each illustrate antifungal properties of alkoxylated or alkenoxylated citrate-containing polymers according to some embodiments described herein.
Figure 8B:
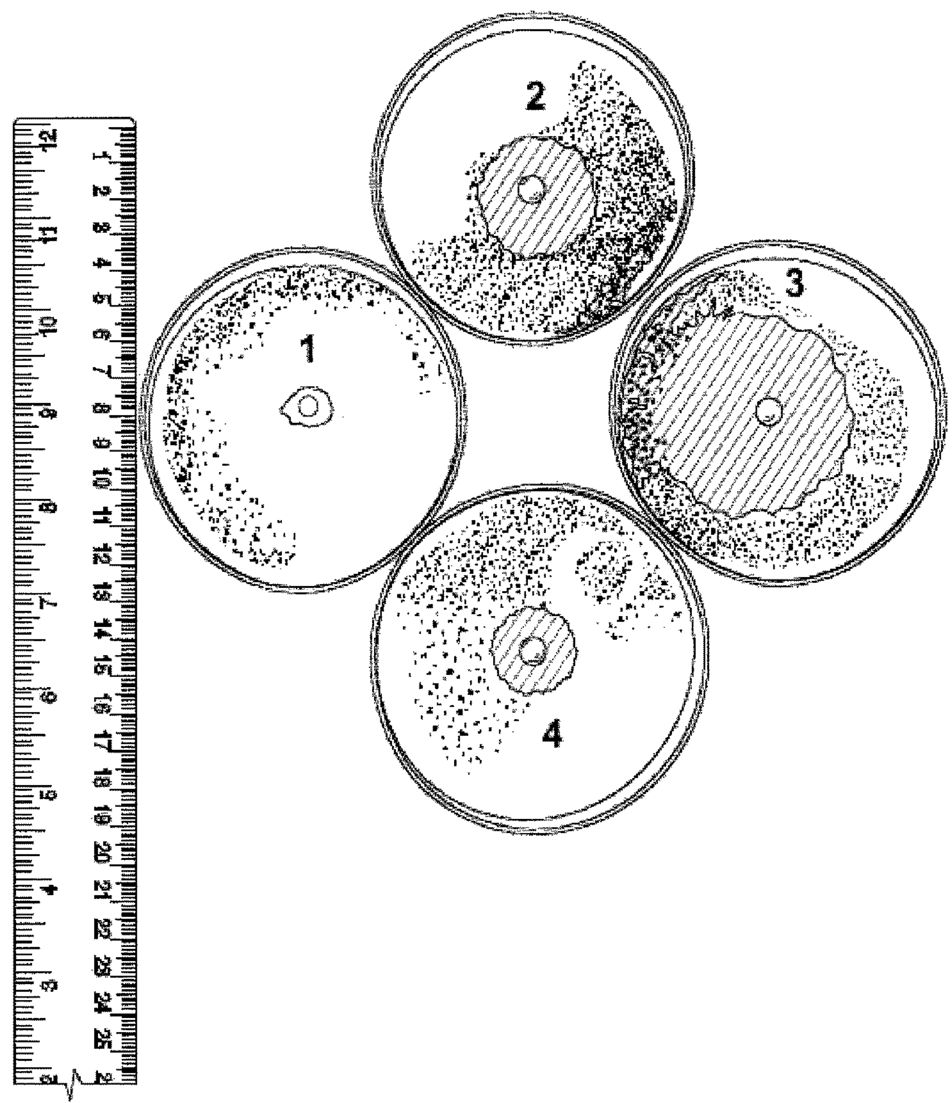

FIG. 8 shows anti-fungal performance of AbAf iCMBAs against *C. albicans*. Fungal survival ratios after direct exposure to cross-linked AbAf iCMBAs, iC-$P_{200}D_{0.3}$ PI 8 wt %, and PEGDA/HEMA (w/w=1/1, as control) for 3 hrs ($p<0.01$) are shown in FIG. 8**A. Inhibition halos of cross-linked hydrogels to *C. albicans* after incubation at 37° C. for 24 hrs are shown in FIG. 8B. Note that 1. PEGDA/HEMA (w/w=1/1), 2. iC-$P_{200}D_{0.3}$ PI 8 wt %, 3. AiC-$P_{2/4(1/1)}D_{0.3}$ PI 8 wt %, and 4. AiC-$P_{2/4(1/1)}D_{0.3}$ SN 0.15 g/mL.

Figure 9A:
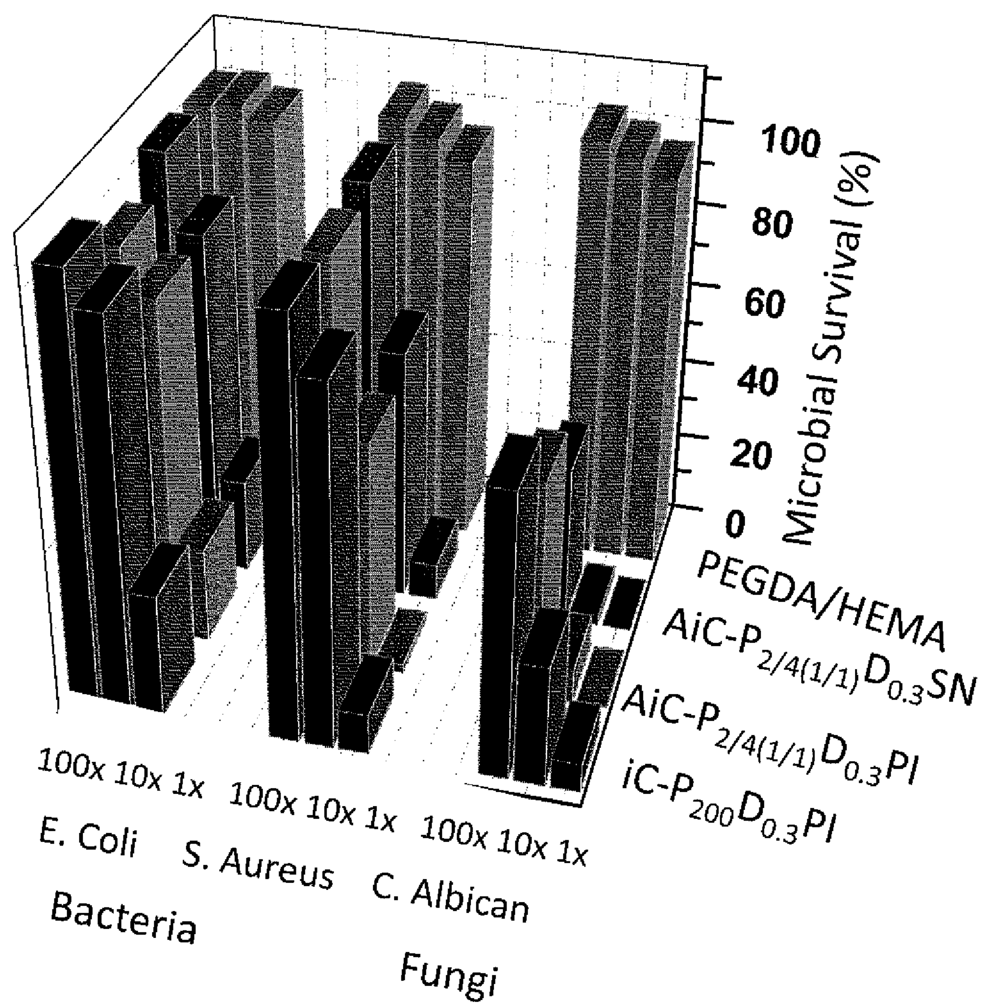
FIGS. 9A and 9B each illustrate long-term antimicrobial properties of alkoxylated or alkenoxylated citrate-containing polymers according to some embodiments described herein.
Figure 9B:
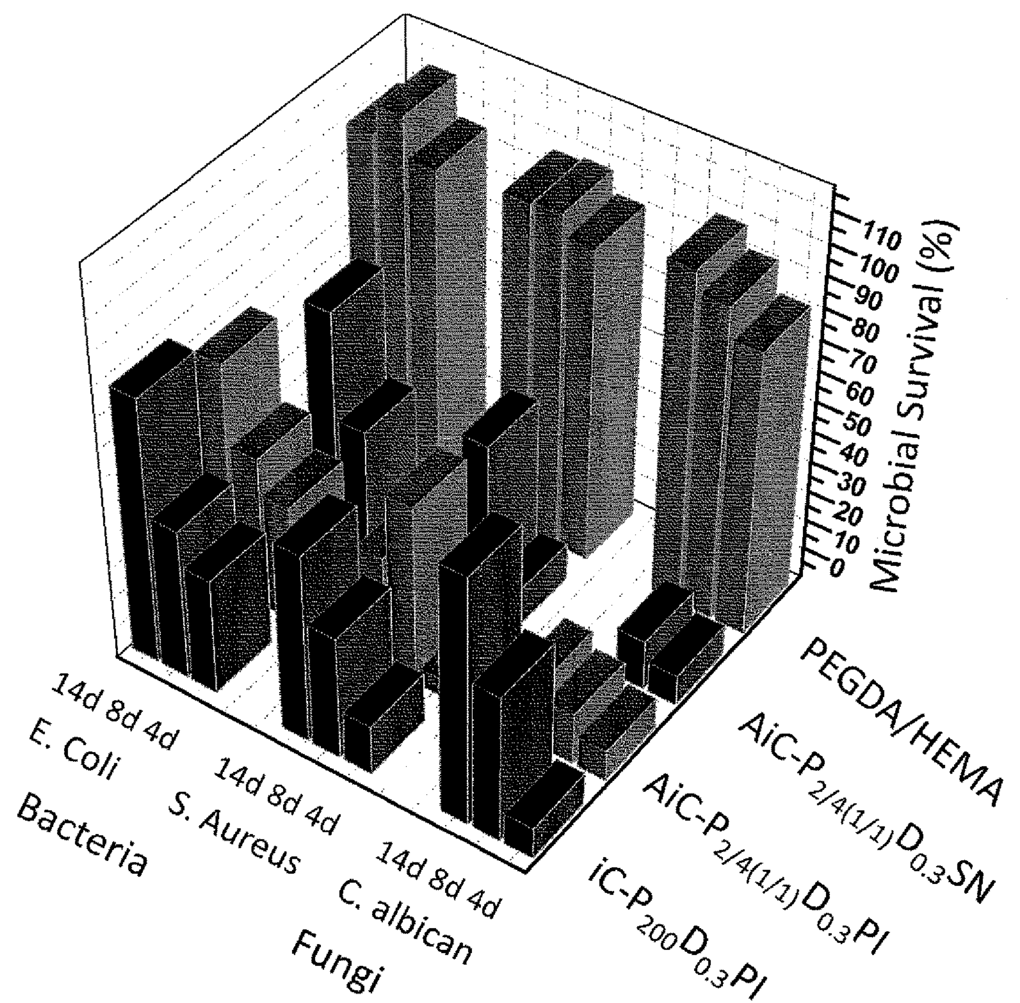

FIGS. 9A-9B depicts a long-term anti-microbial study. Anti-fungal and anti-bacterial performance of degradation products (FIG. 9A) and release solutions (FIG. 9B) of cross-linked hydrogels were used as follows: iC-$P_{200}D_{0.3}$ PI 8 wt %, AiC-$P_{2/4(1/1)}D_{0.3}$ PI 8 wt %, AiC-$P_{2/4(1/1)}D_{0.3}$ SN 0.15 g/mL and PEGDA/HEMA (w/w=1/1, as control)

Figure 11A:
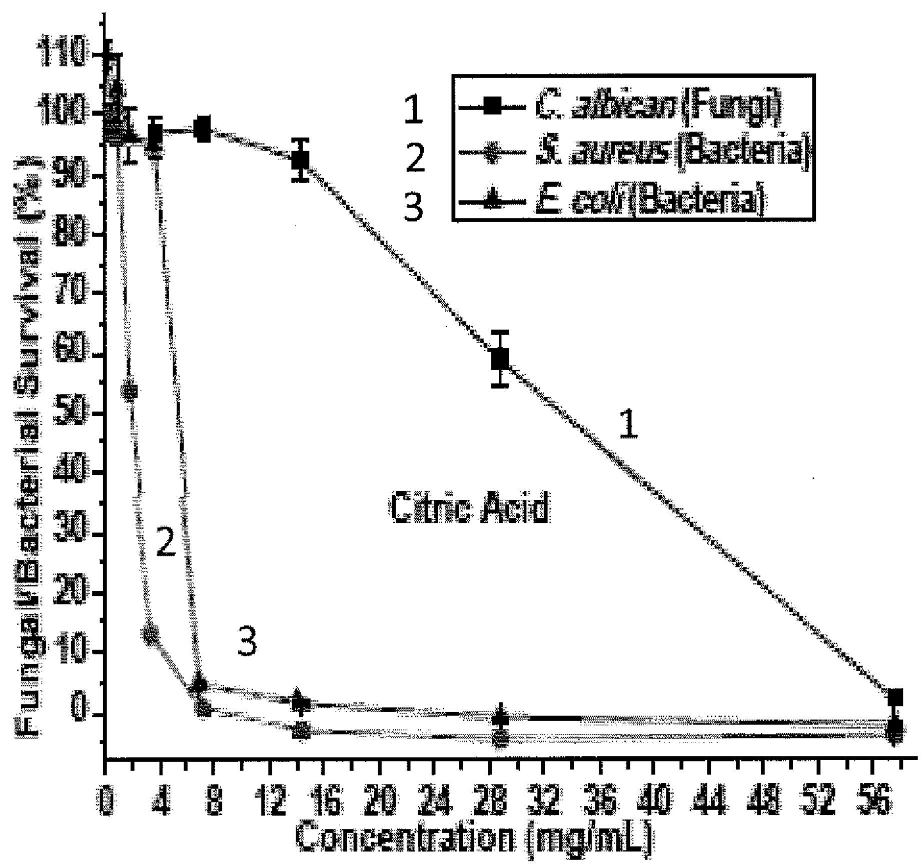
FIGS. 11A, 11B, 11C, and 11D each illustrate antimicrobial properties of components of compositions according to some embodiments described herein.
Figure 11B:
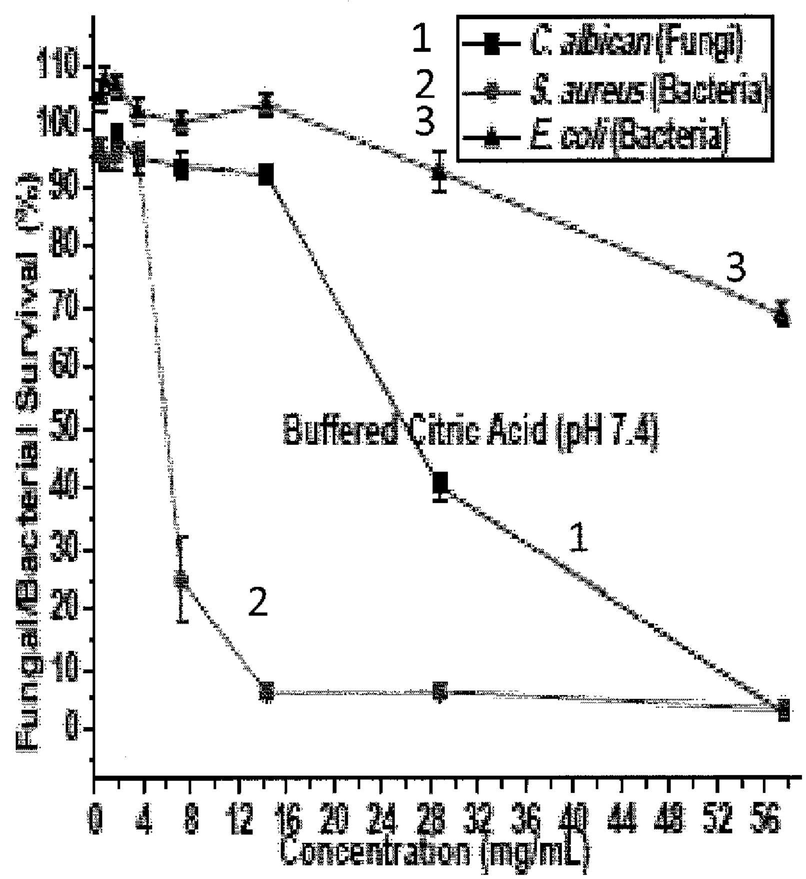
Figure 11C:
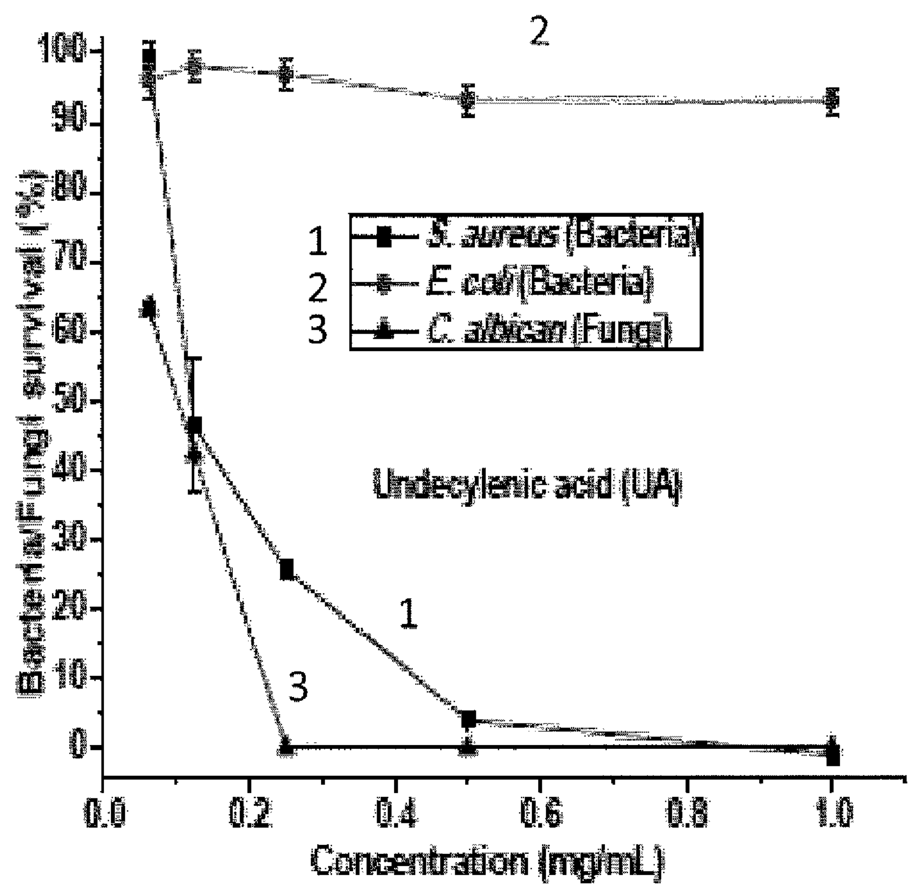
Figure 11D:
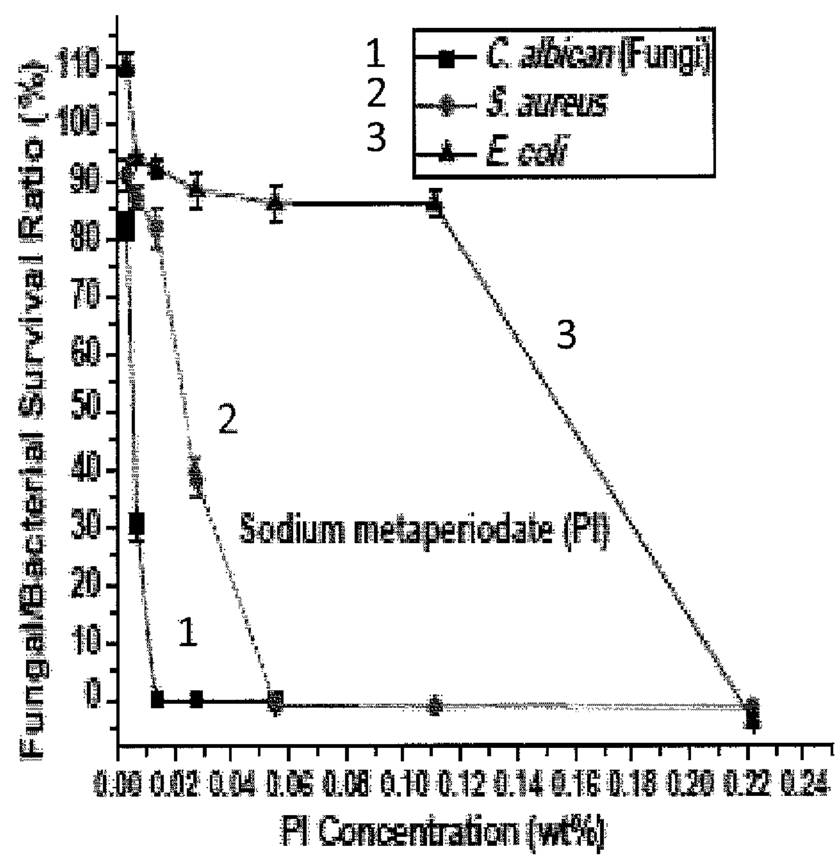
Figure 12A:
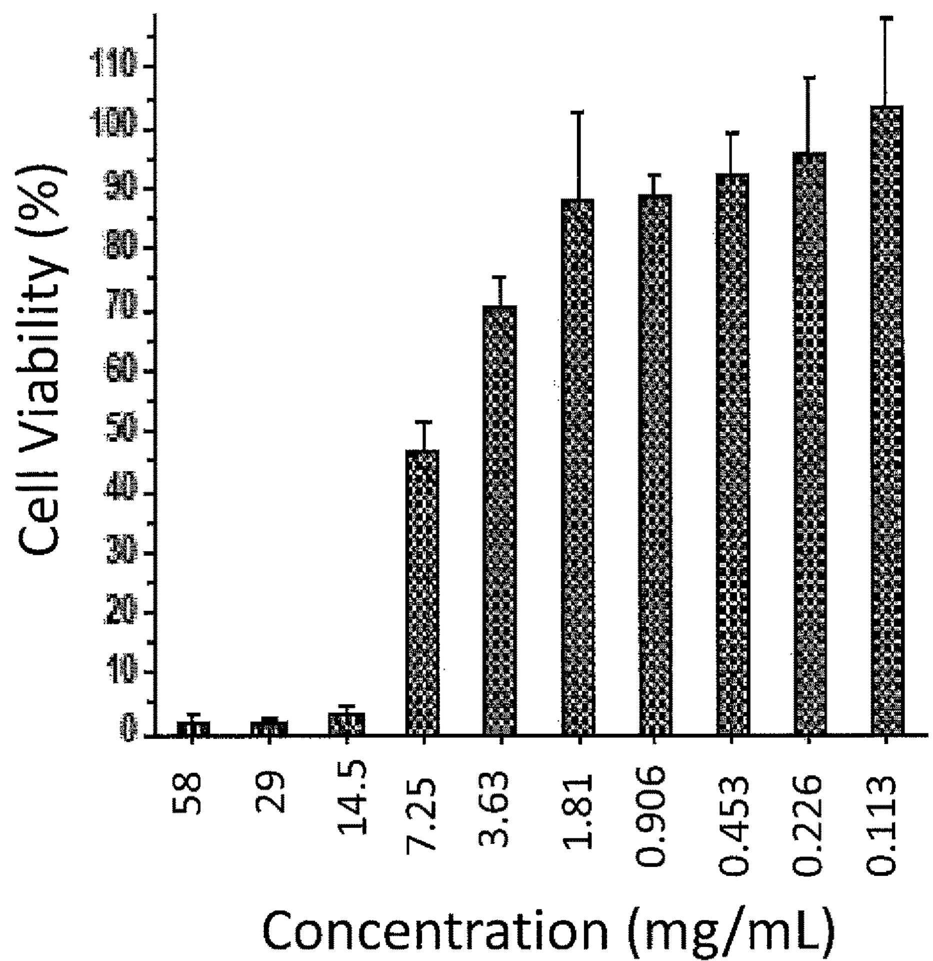
FIGS. 12A and 12B each illustrate anti-microbial properties of components of compositions according to some embodiments described herein.
Figure 12B:
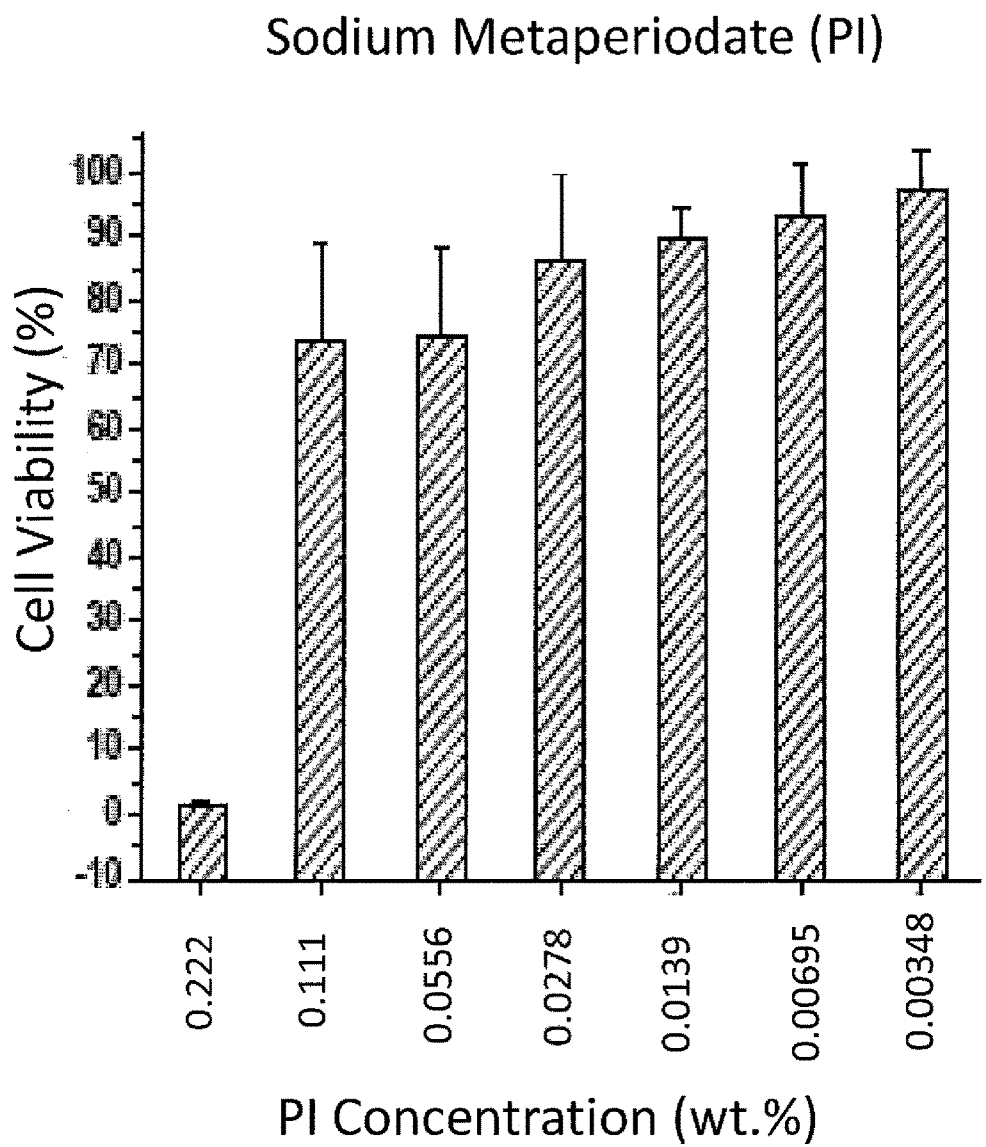

FIGS. 11A-11D depict the anti-bacterial properties of the components of iC-$P_{200}D_{0.3}$ PI 8 wt % and AiC-$P_{2/4(1/1)}D_{0.3}$ PI 8 wt %, including citric acid (CA) sodium periodate (PI), and 10-undecylenic acid (UA). FIG. 11A depicts the anti-bacterial properties of CA; FIG. 11B depicts the anti-bacterial properties of CA buffered to pH 7.4; FIG. 11C depicts the anti-bacterial properties of UA; and FIG. 11D depicts the anti-bacterial properties of PI. FIGS. 12A-12B depict cell viability when varying concentrations of CA or PI are present.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A composition comprising:

a polymer or oligomer formed from one or more monomers of Formula (A1), one or more monomers of Formula (B1), (B2), or (B3), and optionally, a monomer according to Formula (A2):

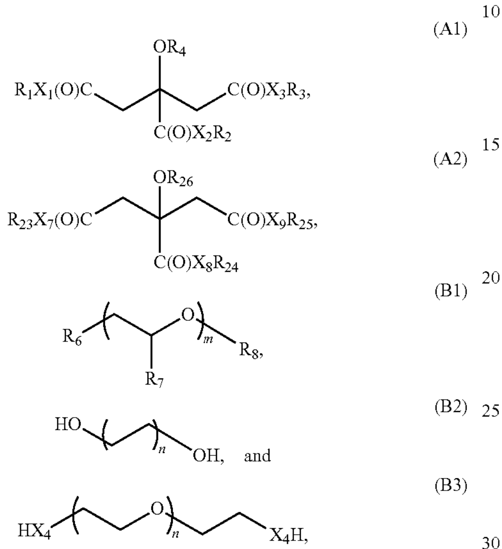

wherein $X_1$, $X_2$, $X_3$, $X_4$, $X_7$, $X_8$, and $X_9$ are each independently —O— or —NH—;

$R_1$, $R_2$, and $R_3$ are independently —H, a C1 to C22 alkyl or alkenyl group, or $M^+$;

$R_4$ is —C(O)$R_5$;

$R_5$ is a C4 to C22 alkyl or alkenyl group;

$R_{23}$, $R_{24}$, and $R_{25}$ are independently —H, a C1 to C22 alkyl or alkenyl group, or $M^+$;

$R_{26}$ is —H or $M^+$;

$M^+$ is a monovalent metal cation;

$R_6$ is —H, —NH, —OH, —$OCH_3$, —$OCH_2CH_3$, —$CH_3$, or —$CH_2CH_3$;

$R_7$ is —H, or a C1 to C22 alkyl or alkenyl group;

$R_8$ is —H, a C3 to C22 alkyl or alkenyl group, —$CH_2CH_2OH$, or —$CH_2CH_2NH_2$; and n and m are independently integers ranging from 1 to 20.

2. The composition of claim 1, wherein the polymer or oligomer is formed from one or more monomers of Formula (A1), one or more monomers of Formula (B1), (B2), or (B3), and one or more monomers of Formula (C), Formula (D1), Formula (D2), Formula (D3), Formula (D4), Formula (E1), Formula (E2), Formula (F), Formula (G), Formula (H1), Formula (H2), Formula (H3), Formula (I1), Formula (I2), Formula (I3), Formula (I4), Formula (I5), and/or Formula (I6), and optionally one or more monomers of Formula (A2):

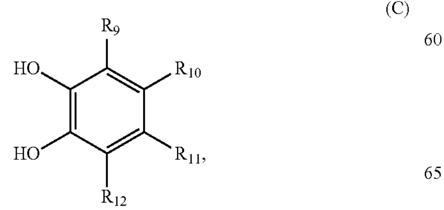

-continued

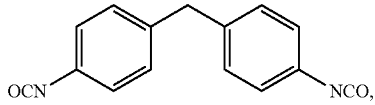

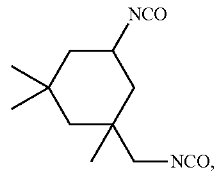

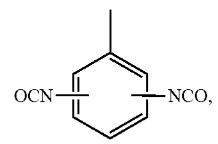

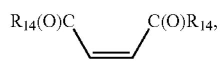

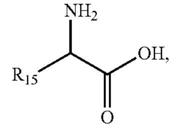

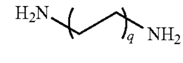

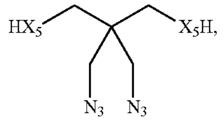

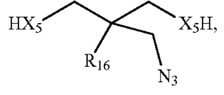

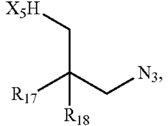

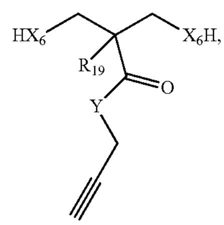

-continued

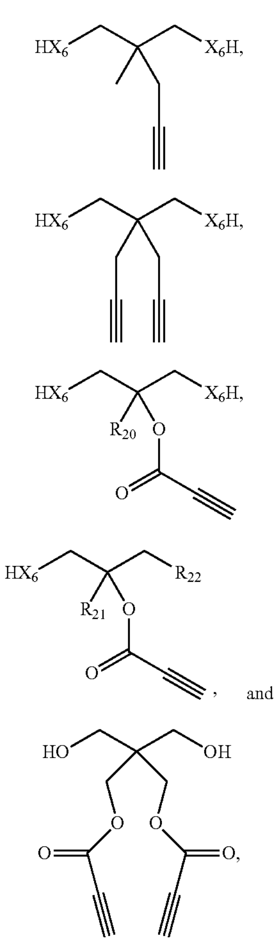

wherein $R_9$, $R_{10}$, $R_{11}$, and $R_{12}$ are each independently —H, —OH, —$CH_2(CH_2)_xNH_2$, —$CH_2(CHR_{13})NH_2$, —$CH_2(CH_2)_xOH$, —$CH_2(CHR_{13})OH$, or —$CH_2(CH_2)_xCOOH$;

$R_{13}$ is —COOH or —$(CH_2)_yCOOH$;

x is an integer ranging from 0 to 10;

y is an integer ranging from 1 to 10;

p is an integer ranging from 1 to 10;

$R_{14}$ is —OH, —$OCH_3$, —$OCH_2CH_3$, or —Cl;

$R_{15}$ is an amino acid side chain;

q is an integer ranging from 1 to 20;

$X_5$ is —O— or —NH—;

$R_{16}$ is —$CH_3$ or —$CH_2CH_3$;

$R_{17}$ and $R_{18}$ are each independently —$CH_2N_3$, —$CH_3$, or —$CH_2CH_3$;

$X_6$ and Y are each independently —O— or —NH—;

$R_{19}$ and $R_{20}$ are each independently —$CH_3$ or —$CH_2CH_3$;

$R_{21}$ is —O(CO)C≡CH, —$CH_3$, or —$CH_2CH_3$; and $R_{22}$ is —$CH_3$, —OH or —$NH_2$.

3. The composition of claim 1, wherein the polymer or oligomer is formed from one or more monomers of Formula (A1), one or more monomers of Formula (B1), (B2), or (B3), one or more monomers of Formula (C), and optionally one or more monomers of Formula (A2):

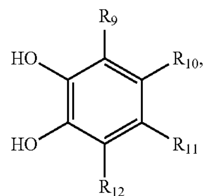

wherein $R_9$, $R_{10}$, $R_{11}$, and $R_{12}$ are independently —H, —$CH_2(CH_2)_xNH_2$, —$CH_2(CHR_{13})NH_2$, or —$CH_2(CH_2)_xCOOH$;

$R_{13}$ is —COOH or —$(CH_2)_yCOOH$;

x is an integer ranging from 0 to 10; and y is an integer ranging from 1 to 10.

4. The composition of claim 2, wherein the polymer or oligomer is formed from one or more monomers comprising maleic acid, maleic anhydride, or fumaric acid.

5. The composition of claim 3, wherein at least one monomer of Formula (C) is dopamine, L-DOPA, D-DOPA or 3,4-dihydroxyhydrocinnamic acid.

6. The composition of claim 1, wherein the polymer or oligomer is formed from one or more monomers comprising a diamine.

7. The composition of claim 6, wherein the diamine has the structure of Formula (G):

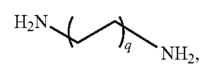

wherein q is an integer ranging from 1 to 20.

8. The composition of claim 1, wherein the polymer or oligomer is formed from one or more monomers comprising one or more alkyne moieties or one or more azide moieties.

9. The composition of claim 8, wherein the one or more monomers comprising one or more azide moieties comprises a monomer of Formula (H1), (H2), or (H3):

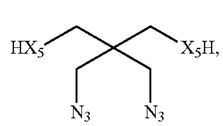

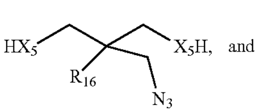

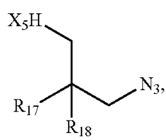

wherein $X_5$ is —O— or —NH—;

$R_{16}$ is —$CH_3$ or —$CH_2CH_3$; and $R_{17}$ and $R_{18}$ are each independently —$CH_2N_3$, —$CH_3$, or —$CH_2CH_3$.

10. The composition of claim 8, wherein the one or more monomers comprising one or more alkyne moieties comprises a monomer of Formula (I1), (I2), (I3), (I4), (I5) or (I6):

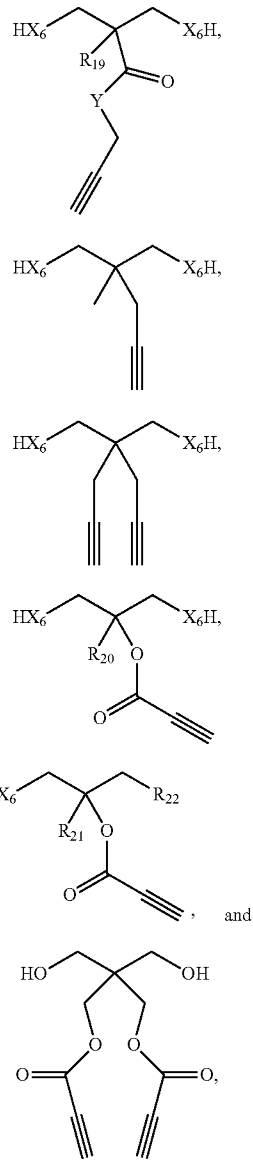

wherein $X_6$ and Y are each independently —O— or —NH—;

$R_{19}$ and $R_{20}$ are each independently —$CH_3$ or —$CH_2CH_3$;

$R_{21}$ is —O(CO)C≡CH, —$CH_3$, or —$CH_2CH_3$; and $R_{22}$ is —$CH_3$, —OH or —$NH_2$.

11. The composition of claim 8, wherein the one or more monomers comprising one or more alkyne moieties or one or more azide moieties comprises a peptide, polypeptide, nucleic acid, or polysaccharide.

12. The composition of claim 1, wherein the composition further comprises a drug dispersed in the polymer or oligomer.

13. The composition of claim 3, wherein the composition further comprises at least one oxidant.

14. The composition of claim 13, wherein the oxidant is at least one of sodium periodate ($NaIO_4$) or silver nitrate ($AgNO_3$), and wherein the composition further comprises at least one reduced form of the oxidant.

15. The composition of claim 1, wherein the polymer or oligomer is crosslinked to form a polymer network.

16. The composition of claim 1, wherein the composition further comprises nanoparticles dispersed in the polymer or oligomer.

17. A method of treating a microbial infection comprising:

disposing a composition of claim 1 in or on a biological environment.

18. The method of claim 17, wherein the biological environment is a surface of skin of a living patient.

19. The method of claim 17, wherein the microbial infection comprises both a bacterial infection and a fungal infection, and the method further comprises:

killing at least 10% of bacteria of the bacterial infection; and killing at least 10% of fungi of the fungal infection.

20. The method of claim 17, wherein microbial proliferation in the biological environment is reduced by at least 50% compared to a negative control.

* * * * *